US009439935B2

(12) United States Patent
Bird et al.

(10) Patent No.: US 9,439,935 B2
(45) Date of Patent: Sep. 13, 2016

(54) RECOMBINANT RIFT VALLEY FEVER (RVF) VIRUSES AND METHODS

(71) Applicant: The United States of America as represented by the Secretary of the Department of Health and Human Services, Centers for Disease Control and Prevention, Washington, DC (US)

(72) Inventors: Brian H. Bird, Atlanta, GA (US); Cesar G. Albarino, Atlanta, GA (US); Stuart T. Nichol, Atlanta, GA (US); Thomas G. Ksiazek, Galveston, TX (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 11 days.

(21) Appl. No.: 14/163,058

(22) Filed: Jan. 24, 2014

(65) Prior Publication Data

US 2014/0134207 A1 May 15, 2014

Related U.S. Application Data

(62) Division of application No. 12/809,561, filed as application No. PCT/US2008/087023 on Dec. 16, 2008, now Pat. No. 8,673,629.

(60) Provisional application No. 61/016,065, filed on Dec. 21, 2007, provisional application No. 61/042,987, filed on Apr. 7, 2008.

(51) Int. Cl.
*A61K 39/12* (2006.01)
*C12N 7/00* (2006.01)
*A61K 35/76* (2015.01)
*A61K 39/00* (2006.01)

(52) U.S. Cl.
CPC .............. *A61K 35/76* (2013.01); *A61K 39/12* (2013.01); *C12N 7/00* (2013.01); *A61K 39/00* (2013.01); *A61K 2039/525* (2013.01); *A61K 2039/5254* (2013.01); *C12N 2760/12211* (2013.01); *C12N 2760/12221* (2013.01); *C12N 2760/12234* (2013.01)

(58) Field of Classification Search
CPC ............. A61K 2039/5254; A61K 2039/5258; C12N 2760/12262; C12N 2760/12221; C12N 2760/16134; C12N 2710/14143; C12N 2760/16122; C12N 2760/18522; C07K 16/10; C07K 14/005; C07K 2319/03; G01N 2333/175; A01K 67/0339
See application file for complete search history.

(56) References Cited

U.S. PATENT DOCUMENTS

| 4,735,800 A * | 4/1988 | Collett ................. C07K 14/005 424/186.1 |
| 7,312,036 B2 * | 12/2007 | Sampath .................. C12Q 1/70 435/6.16 |
| 8,084,248 B2 * | 12/2011 | Makino et al. ............ 435/320.1 |
| 2003/0224017 A1 | 12/2003 | Samal et al. |
| 2007/0122431 A1 | 5/2007 | Makino et al. |

OTHER PUBLICATIONS

Muller et al. Nucleic acid, 1991, vol. 19, p. 5433.*
Albarilio et al., "A Shared Transcription Termination Signal on Negative and Ambisense RNA Genome Segments of Rift Valley Fever, Sandfly Fever Sicilian, and Toscana Viruses," Journal of Virology 81(10):5246-5256, May 2007.
Baskerville et al., "Comparison of the pathogenicity for pregnant sheep of Rift Valley fever virus and a live attenuated vaccine," Research in Veterinary Science 52:307-311, 1992.
Billecocq et al., "NSs Protein of Rift Valley Fever Virus Blocks Interferon Production by Inhibiting Host Gene Transcription," Journal of Virology 78(18):9798-9806, Sep. 2004.
Bird et al., "Highly Sensitive and Broadly Reactive Quantitative Reverse Transcription-PCR Assay for High-Throughput Detection of Rift Valley Fever Virus," Journal of Clinical Microbiology 45(11):3506-3513, Nov. 2007.
Bird et al., "Complete Genome Analysis of 33 Ecologically and Biologically Diverse Rift Valley Fever Virus Strains Reveals Widespread Virus Movement and Low Genetic Diversity Due to Recent Common Ancestry," Journal of Virology 81(6 :2805-2816, Mar. 2007.
Bird et al., "Rift Valley fever virus lacking NSm proteins retains high virulence in vivo and may provide a model of human delayed onset neurologic disease," Virology 362(1):10-15, May 25, 2007.
Bird et al., "Rift Valley Fever Virus Lacking the NSs and NSm Genes is Highly Attenuated, Confers Protective Immunity from Virulent Virus Challenge, and Allows for Differential Identification of Infected and Vaccinated Animals," *J. Virol.* 82(6):2681-2691, 2008.
Blakqori et al., "Efficient cDNA-Based Rescue of La Crosse Bunyaviruses Expressing or Lacking the Nonstructural Protein NSs," Journal of Virology 79(16):10420-10428, Aug. 2005.

(Continued)

*Primary Examiner* — Bao Li
(74) *Attorney, Agent, or Firm* — Klarquist Sparkman, LLP

(57) ABSTRACT

Described herein are recombinant RVF viruses comprising deletions in one or more viral virulence genes, such as NSs and NSm. The recombinant RVF viruses, generated using a plasmid-based reverse genetics system, can be used as vaccines to prevent infection of RVF virus in livestock and humans. As described herein, the recombinant RVF viruses grow to high titers, provide protective immunity following a single injection and allow for the differentiation between vaccinated animals and animals infected with wild-type RVF virus.

10 Claims, 9 Drawing Sheets

(56) References Cited

OTHER PUBLICATIONS

Bouloy et al., "Genetic Evidence for an Interferon-Antagonistic Function of Rift Valley Fever Virus Nonstructural Protein NSs," Journal of Virology 75(3):1371-1377, Feb. 2001.

Bridgen et al., "Rescue of a segmented negative-strand RNA virus entirely from cloned complementary DNAs," Proc. Natl. Acad. Sci. 93:15400-15404, Dec. 1996.

Buchholz et al., "Generation of Bovine Respiratory Syncytial Virus (BRSV) from cDNA: BRSV NS2 Is Not Essential for Virus Replication in Tissue Culture, and the Human RSV Leader Region Acts as a Functional BRSV Genome Promoter," Journal of Virology 73(1):251-259, Jan. 1999.

Gerrard et al., "The NSm proteins of Rift Valley fever virus are dispensable for maturation, replication and infection," Virology 359:459-465, 2007.

Ikegami et al., "Characterization of Rift Valley Fever Virus Transcriptional Terminations," Journal of Virology 81(16):8421-8438, Aug. 2007.

Ikegami et al., "Rescue of Infectious Rift Valley Fever Virus Entirely from cDNA, Analysis of Virus Lacking the NSs Gene, and Expression of a Foreign Gene," Journal of Virology 80(6):2933-2940, Mar. 2006.

Ikegami et al., "Rift Valley Fever Virus Nonstructural Protein NSs Promotes Viral RNA Replication and Transcription in a Minigenome System," Journal of Virology 79(9):5606-5615, May 2005.

Le May et al., "TFIIH Transcription Factor, a Target for the Rift Valley Hemorrhagic Fever Virus " Cell 116:541-550 Feb. 20, 2004.

Lopez et al., "The L Protein of Rift Valley Fever Virus Can Rescue Viral Ribonucleoproteins and Transcribe Synthetic Genome-Like RNA Molecules," Journal of Virology 69(7):3972-3979, Jul. 1995.

Morrill et al., "Pathogenicity and neurovirulence of a mutagen-attenuated Rift Valley fever vaccine in rhesus monkeys," Vaccine 21:2994-3002, 2003.

Morrill et al., "Pathogenicity and immunogenicity of a mutagen-attenuated Rift Valley fever virus immunogen in pregnant ewes," Am J Vet Res 48(7):1042-1047, Jul. 1987.

Pittman et al., "Immunogenicity of an inactivated Rift Valley fever vaccine in humans: a 12-year experience," Vaccine 18:181-189, 2000.

Spik et al., "Immunogenicity of Combination DNA Vaccines for Rift Valley Fever Virus, Tick-Borne Encephalitis Virus, Hantaan Virus, and Crimean Congo Hemorrhagic Fever Virus," *Vaccine*, vol. 24:4657-4666, 2006.

Suzich et al., "Expression Strategy of a Phlebovirus: Biogenesis of Proteins from the Rift Valley Fever Virus M Segment," Journal of Virology 64(4):1549-1555, Apr. 1990.

Vialat et al., "The S Segment of Rift Valley Fever Phlebovirus (*Bunyaviridae*) Carries Determinants for Attenuation and Virulence in Mice," Journal of Virology 74(3):1538-1543, Feb. 2000.

Walsh et al., "Development of a Genetically Marked Recombinant Rinderpest Vaccine Expressing Green Fluorescent Protein," *J. General Virol.*, vol. 81:709-718, 2000.

Won et al., "NSm and 78-Kilodalton Proteins of Rift Valley Fever Virus Are Nonessential for Viral Replication in Cell Culture," Journal of Virology 80(16):8274-8278, Aug. 2006.

Won et al., "NSm Protein of Rift Valley Fever Virus Suppresses Virus-Induced Apoptosis," Journal of Virology 81(24):13335-13345, Dec. 2007.

\* cited by examiner

FIG. 1A Recombinant RVF viruses

FIG. 1B Live infected cells

FIG. 1C Fixed and gamma-irradiated cells

FIG. 3A Serum from WT survivors rats
FIG. 3B Serum from vaccinated rats
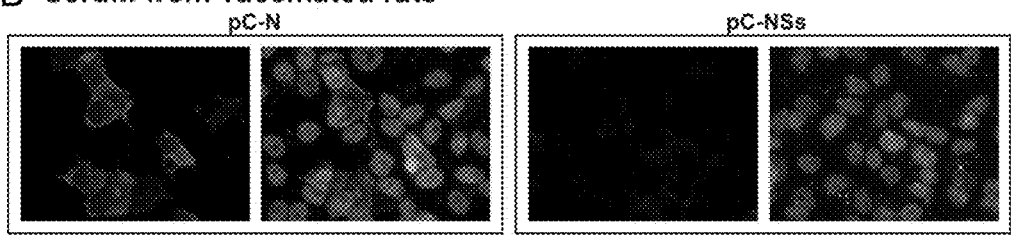
FIG. 3C Serum from control rats
FIG. 3D Serum from naturally infected goats

FIG. 4A  Pilot Study: Day 21 post-immunization

| Inoculum | # animals | Vacc. Dose (PFU) | RVF IgG SUM$_{OD}$ mean ± (SEM) | PRNT$_{80}$ mean ± (SEM) | RVF viremia (PFU/mL eq.) post-vaccination (day 1-4) |
|---|---|---|---|---|---|
| rRVF-ΔNSs:GFP | 9 | 1x10$^3$ | 2.14 ± 0.12*§ | 1:1480 ± (631) | 0.0 |
| rRVF-ΔNSs:GFP-ΔNSm | 9 | 1x10$^3$ | 1.24 ± 0.06*§ | 1:280 ± (120) | 0.0 |
| Neg. Control | 3 | 0 | -0.08 ± 0.06 | 1:10 ± (0.0) | 0.0 |

FIG. 4B  Challenge Study: Day 26 post-immunization

| Inoculum | # animals | Vacc. Dose (PFU) | RVF IgG SUM$_{OD}$ mean ± (SEM) | PRNT$_{80}$ mean ± (SEM) | RVF viremia (PFU/mL eq.) post-vacc. (d1-7) | Peak post-challenge (day) | # Surviving Challenge |
|---|---|---|---|---|---|---|---|
| rRVF-ΔNSs:GFP | 10 | 1x10$^3$ | 4.10 ± (0.12)* | 1:640 (0.0) | 0.0 | 10 animals = 0.0* | 10/10* |
| rRVF-ΔNSs:GFP | 10 | 1x10$^4$ | 4.79 ± (0.11)* | 1:7040 (3200) | 0.0 | 9 = 0.0* 1 = 1.5x10$^1$ (d4)* | 10/10* |
| rRVF-ΔNSs:GFP-ΔNSm | 10 | 1x10$^3$ | 3.94 ± (0.12)* | 1:1120 (733) | 0.0 | 9 = 0.0* 1 = 1.1x10$^2$ (d3)* | 10/10* |
| rRVF-ΔNSs:GFP-ΔNSm | 10 | 1x10$^4$ | 4.54 ± (0.13)* | 1:640 (0.0) | 0.0 | 9 = 0.0* 1 = 7.0x10$^1$ (d3)* | 10/10* |
| Neg. Control | 5 | 0 | -0.02 ± (0.09) | 1:5 (2.9) | 0.0 | 3 = 3.4x10$^2$ (d3) 2 = 1.6x10$^2$ (d4) | 2/5 |

SEQUENCE LISTING

<160> NUMBER OF SEQ ID NOS: 15

<210> SEQ ID NO 1
<211> LENGTH: 1690
<212> TYPE: DNA
<213> ORGANISM: Rift Valley fever virus

<400> SEQUENCE: 1

```
acacaaagac cccctagtgc ttatcaagta tatcatggat tactttcctg tgatatctgt      60
tgatttgcag agtggtcgtc gtgttgtgtc agtggagtac tttagaggag atggtcctcc     120
caggatacct tattctatgg ttgggccctg ttgtgtcttt ctcatgcacc atcgtcctag     180
tcacgaggtt cgcttgcgat tctctgattt ctacaatgtc ggagaattcc cataccgagt     240
cggacttgga gactttgcat caaacgttgc acctccacca gcgaagcctt ttcagagact     300
tattgatcta ataggccata tgactcttag tgatttcaca aggttcccca atctgaaaga     360
agccatatcc tggcctcttg gagaaccctc actggctttc tttgacctaa gctctactag     420
agtgcatagg aatgatgaca ttagaaggga tcagattgcc actctagcaa tgaggagttg     480
caagatcacc aatgatctag aggactcctt tgttggctta cacaggatga tagcgactga     540
ggccatcctc agagggattg acctgtgcct gttgccaggc tttgatctca tgtatgaggt     600
tgctcacgta cagtgcgttc ggcttctgca agcagcaaaa gaggacattt ctaatgctgt     660
agttccaaac tcagccctca ttgttcttat ggaggagagc ctgatgctgc gctcatcact     720
tcccagcatg atggggagaa acaactggat tccagttatt cctccaatcc cagatgttga     780
gatggaatca gaggaggaga gtgatgatga tggatttgtt gaggttgatt agaggttaag     840
gctgccccac cccccacccc ccaatcccga ccgtaacccc aactcccctt cccccaacc     900 ccctgggcag ccacttaggc tgctgtcttg taagcctgag cggctgccat gacagcagct     960
gacggcttcc cattagaatc cacaagtcca aaggctttca agaattctct cctcttctca    1020
tggcttataa agttgctatt cactgctgca ttcattggct gcgtgaacgt tgcagcaacc    1080
tcctcttttg ttctacctcg gaggtttggg ttgatgaccc gggagaactg cagcagatac    1140
agagagtgag catctaatat tgcccttaga tagtctcctg gtagagaagg atccaccatg    1200
ccagcaaagc tgggtgcat catatgcctt gggtatgcag gggataggcc gtccatggta    1260
gtcccagtga caggaagcca ctcactcaag acgaccaaag cctggcatgt ccagccagcc    1320
agggcggcag caactcgtga tagagtcaac tcatcccggg aaggattccc ttcctttagc    1380
```

| | |
|---|---|
| ttatacttgt tgatgagagc ctccacagtt gctttgcctt ctttcgacat tttcatcatc | 1440 |
| atcctcctgg gcttgttgcc acgagttaga gccagaacaa tcattttctt ggcatccttc | 1500 |
| tcccagtcag ccccaccata ctgctttaag agttcgataa ctctacgggc atcaaaccct | 1560 |
| tgataagcaa actctcggac ccactgttca atctcattgc ggtccactgc ttgagcagca | 1620 |
| aactggatcg caagctcttg atagttgtcc attattgtaa tagtgtttgt atctctaggg | 1680 |
| agctttgtgt | 1690 |

<210> SEQ ID NO 2
<211> LENGTH: 3885
<212> TYPE: DNA
<213> ORGANISM: Rift Valley fever virus

<400> SEQUENCE: 2

| | |
|---|---|
| acacaaagac ggtgcattaa atgtatgttt tattaacaat tctaatctcg gttctggtgt | 60 |
| gtgaagcggt tattagagtg tctctaagct ccacaagaga agagacctgc tttggtgact | 120 |
| ccactaaccc agagatgatt gaaggagctt gggattcact cagagaggag gagatgccgg | 180 |
| aggagctctc ctgttctata tcaggcataa gagaggttaa gacctcaagc caggagttat | 240 |
| acagggcatt aaaagccatc attgctgctg atggcttgaa caacatcacc tgccatggta | 300 |
| aggatcctga ggacaagatt ccctcataaa agggtcctcc tcacaaaaag cgggtgggga | 360 |
| tagttcggtg tgagagacga agagatgcta agcaaatagg gagagaaacc atggcaggga | 420 |
| ttgcaatgac agtccttcca gccttagcag ttttttgcttt ggcacctgtt gtttttgctg | 480 |
| aagacccca tctcagaaac agaccaggga aggggcacaa ctacattgac gggatgactc | 540 |
| aggaggatgc cacatgcaaa cctgtgacat atgctggggc atgtagcagt tttgatgtct | 600 |
| tgcttgaaaa ggaaaatttt cccctttcc agtcgtatgc tcatcataga actctactag | 660 |
| aggcagttca cgacaccatc attgcaaagg ctgatccacc tagctgtgac cttcagagtg | 720 |
| ctcatgggaa cccctgcatg aaagagaaac tcgtgatgaa gacacactgt ccaaatgact | 780 |
| accagtcagc tcattacctc aacaatgacg ggaaaatggc ttcagtcaag tgccctccta | 840 |
| agtatgagct cactgaggac tgcaacttttt gtaggcagat gacaggtgct agcctgaaga | 900 |
| agggtctta tcctctccaa gacttgtttt gtcagtcaag tgaggatgat ggatcaaaat | 960 |
| taaaaacaaa aatgaaaggg gtctgcgaag tgggggttca agcactcaaa agtgtgatg | 1020 |
| gccaactcag cactgcacat gaggttgtgc cctttgcagt gtttaagaac tcaaagaagg | 1080 |
| tttatcttga taagcttgac cttaagactg aggagaatct gctaccagac tcatttgtct | 1140 |
| gtttcgagca taagggacag tacaaaggaa caatggactc tggtcagact aagagggagc | 1200 |
| tcaaaagctt tgatatctct cagtgcccca gattggagg acatggtagt aagaagtgca | 1260 |
| ctggggacgc agcatttttgc tctgcttatg agtgcactgc tcagtacgcc aatgcctatt | 1320 |
| gttcacatgc taatgggtca gggattgtgc agatacaagt atcaggggtc tggaagaagc | 1380 |
| ctttatgtgt agggtatgag agagtggttg tgaagagaga actctctgcc aagcccatcc | 1440 |
| agagagttga gccttgcaca acttgtataa ccaaatgtga gcctcatgga ttggttgtcc | 1500 |
| gatcaacagg gttcaagata tcatcagcag ttgcttgtgc tagcggagtt tgcgtcacag | 1560 |
| gatcgcagag tccttccacc gagattacac tcaagtatcc agggatatcc cagtcttctg | 1620 |
| gggggacat aggggttcac atggcacacg atgatcagtc agttagctcc aaaatagtag | 1680 |
| ctcactgccc tccccaggac ccgtgcttag tgcatggctg catagtgtgt gctcatggcc | 1740 |
| tgataaatta ccagtgtcac actgctctca gtgcctttgt tgttgtgttt gtattcagtt | 1800 |

```
ctattgcaat aatttgttta gctgttcttt atagggtgct taagtgcctg aagattgccc      1860
caaggaaagt tctgaatcca ctaatgtgga tcacagcctt catcagatgg atatataaga      1920
agatggttgc cagagtggca gacaacatta atcaagtgaa cagggaaata ggatggatgg      1980
aaggaggtca gttggttcta gggaaccctg ccctattcc tcgtcatgcc caatcccac        2040 gttatagcac atacctgatg ttattattga ttgtctcata tgcatcagca tgttcagaac      2100
tgattcaggc aagctccaga atcaccactt gctctacaga gggtgttaac accaagtgta      2160
gactgtctgg cacagcattg atcagagcag ggtcagttgg ggcagaggct tgtttgatgt      2220 tgaaggggt caaggaagat caaaccaagt tcttaaagat aaaaactgtc tcaagtgagc       2280
tatcatgcag ggagggccag agttattgga ctgggtcctt tagccctaaa tgtttgagct      2340
caaggagatg ccaccttgtc ggggaatgcc atgtgaatag gtgtctgtct ggagggaca       2400 atgaaacttc agcagagttt tcatttgttg gggaaagcac gaccatgcga gagaataagt      2460
gttttgagca atgtgtgagga tgggggtgtg ggtgtttcaa tgtgaaccca tcttgcttat     2520
ttgtgcacac gtatctgcag tcagttagaa aagaggccct tagagttttt aactgtatcg      2580
actgggtgca taaactcact ctagagatca cagactttga tggctctgtt tcaacaatag      2640
acttgggagc atcatctagc cgtttcacaa actggggttc agttagcctc tcactggacg      2700
cagagggcat ctcaggctca aatagctttt ctttcattga gacccaggc aaagggtatg       2760 caattgttga tgagccattc tcagaaattc ctcggcaagg gttcttgggg gagatcaggt      2820
gcaattcaga gtcctcagtc ctgagtgctc atgaatcatg ccttagggca ccaaaccta       2880 tctcatacaa gcccatgata gatcaattgg agtgcacaac aaatctgatt gatcccttg      2940 ttgtctttga gagggttct ctgccacaga caaggaatga taaaaccttt gcagcttcaa       3000
aaggaaatag aggtgttcaa gctttctcta agggctctgt acaagctgat ctaactctga      3060 tgttgacaa ttttgaggtg gactttgtgg gagcagccgt atcttgtgat gccgccttct       3120
taaatttgac aggttgctat tcttgcaatg caggggccag ggtctgcctg tctatcacat      3180
ccacaggaac tggatctctc tctgcccaca taaggatgg gtctctgcat atagtccttc       3240
catcagagaa tggaacaaaa gaccagtgtc agatactaca cttcactgtg cctgaagtag      3300
aggaggagtt tatgtactct tgtgatggag atgagcggcc tctgttggtg aaggggaccc     3360
tgatagccat tgatccattt gatgataggc gggaagcagg gggggaatca acagttgtga     3420
atccaaaatc tggatcttgg aatttctttg actggttttc tggactcatg agttggtttg     3480
gagggcctct taaaactata ctcctcattt gcctgtatgt tgcattatca attgggctct     3540
ttttcctcct tatatatctt ggaagaacag gcctctctaa aatgtggctt gctgccacta    3600
agaaggcctc atagatcagt acgtgtaaa gcaatgtgt gaaataagta gacacaagca       3660
aacctaatta tgtaagtgtt gtacagatag gtcaaattat tggaatatcc aagcttagaa      3720
acttatgcaa taatacttta gatgtaagct tagttgtaat ttgggtggt ggggtgaggc       3780 agcagcagtc tcaagtgctt gtgaatattc tagttggcgt aatcgtcttt tgccagatta     3840
gctgggaatt aaactaactc tttgaagttg caccggtctt tgtgt                     3885
```

<210> SEQ ID NO 3
<211> LENGTH: 6404
<212> TYPE: DNA
<213> ORGANISM: Rift Valley fever virus

<400> SEQUENCE: 3

```
acacaaaggc gcccaatcat ggattctata ttatcaaaac agctggttga caagactggt    60
tttgttagag tgccaatcaa gcattttgac tgtacaatgc taactctggc acttccaaca   120
tttgatgttt ccaagatggt agatagaatt accatagact tcaatctgga tgatatacaa   180
ggagcatctg aaataggctc aactttgcta ccctccatgt cgatagatgt ggaagatatg   240
gccaattttg ttcacgattt caccttggc cacttagctg acaagactga cagactgtta    300
atgcgtgagt tcccatgat gaatgacggg tttgatcatt tgagccctga catgatcatt    360
aaaactacat ctggcatgta caacatcgtt gagttcacca cctttagggg agatgaaaga   420
ggtgcattcc aggctgccat gactaaactc gctaagtatg aggttccttg tgagaacaga   480
tctcagggca ggactgttgt tctttatgtt gttagtgctt atcggcatgg tgtatggtct   540
aatctggagc tagaggactc tgaagcagag gagatggttt ataggtacag acttgctctt   600
agtgtgatgg atgagctaag gaccttgttc ccagaactgt catccacaga tgaggaacta   660
gggaagactg agagagagtt gctagccatg gtctcctcca tccaaataaa ttggtcagtc   720
acagaatctg tgtttccacc cttcagcaga gaaatgtttg acaggtttag atcctcccct   780
cccgattcag agtatatcac gaggatagtg agcagatgcc tcataaattc tcaagagaaa   840
ctcatcaata gttccttctt tgctgaaggg aatgataagg ctctgagatt ttcaaaaaac   900
gctgaagagt gttccttggc agtagagaga gccttaaatc agtatagagc agaagacaac   960
cttagggacc tcaatgacca caagtcaact attcagctgc ctccctggct gtcctatcat  1020
gatgtcgatg gcaaagatct gtgccctctt cagggattag atgtgagagg ggaccatccc  1080
atgtgcaact tgtggaggga agtggtcacc tctgcaaacc tagaggagat tgagaggatg  1140
cacgatgatg cagcagcaga acttgagttt gctctttcgg gagtaaagga caggccagat  1200
gagagaaaca gataccatag agtccaccta aatatgggct cagatgatag tgtctacata  1260
gctgctttag gagttaatgg aaagaagcat aaagcagaca ctttagtgca acaaatgaga  1320
gacaggagta aacagccttt ctccccagac cacgatgtgg atcacatatc tgaatttctc  1380
tctgcatgct ctagtgactt gtgggcaaca gatgaggacc tgtacaaccc tctctcttgt  1440
gataaagagc ttagattggc agcccagagg attcatcagc catccttgtc agaaaggggt  1500
ttcaatgaga tcataacaga gcactacaaa ttcatgggaa gtaggatagg ttcatggtgc  1560
caaatggtca gcttgatagg agctgagcta tcagcttctg ttaaacaaca tgtcaagcct  1620
aactactttg tgattaaacg actactaggt tctgggattt tcttgctaat caagcccact  1680
tccagcaaaa gccatatatt tgtgtctttt gcaattaagc gctcttgctg ggcctttgat  1740
ctctccactt ccagggtttt caagccctac atagatgctg gggatctgtt agttactgac  1800
tttgtttctt ataagctaag caagcttacc aacctctgca agtgcgtttc attaatggag  1860
tcctccttct cattctgggc agaagcattt ggaattccaa gctggaactt tgttggtgac  1920
ttgttcaggt cttcagactc tgcagcaatg gatgcctcat acatgggcaa actttcttta  1980
ttaaccccttt tggaagacaa agcagcaact gaagagttac agactattgc aagatatata  2040
atcatggagg gctttgtctc gcccccagaa atcccaaaac ctcacaagat gacctctaag  2100
tttcctaagg ttctcaggtc agagctgcag gtttacttat taaactgctt atgcagaact  2160
atccagagaa tagcaggtga gcccttcatt cttaagaaga aggatgggtc tatatcctgg  2220
ggtggcatgt tcaatccttt ttcagggcgt ccactgcttg atatgcaacc actcatcagc  2280
tgttgttaca atggttactt taaaaataaa gaagaagaga ctgagccttc gtcccttcct  2340
gggatgtata agaaaatcat agaacttgag caccttagac cacagtcaga tgccttcttg  2400
```

```
ggttacaaag atccagaact tcccagaatg catgagttca gtgtttccta cttgaaggag    2460
gcttgcaatc atgctaagct agtcttgagg agcctctatg gacagaattt catggagcag    2520
atagacaacc agattattcg agagctcagt gggttgactc tagaaaggtt ggccacactt    2580
aaggccacaa gcaactttaa tgagaattgg tatgtctata aggatgtagc agacaaaaac    2640
tacacaaggg ataaattatt agtgaagatg tcaaatatg cctctgaggg aaagagccta     2700
gctatccaga gtttgagga ttgtatgagg cagatagagt cacaaggatg catgcatatt     2760
tgtttgttta agaaacaaca gcatggaggt ctgagagaga tctatgtgat gggtgcagag    2820
gaaagaattg ttcaatcggt ggtggagaca atagccaggt ccatagggaa gttctttgct    2880
tctgataccc tctgtaaccc cccaataaa gtgaaaattc ctgagacaca tggcatcagg     2940
gcccggaagc aatgtaaggg gcctgtgtgg acttgtgcaa catcagatga tgcaaggaag    3000
tggaaccaag gccattttgt tacaaagttt gccctcatgc tgtgtgagtt cacctctcct    3060
aaatggtggc cgctgatcat tagggggatgc tcaatgttta ccaggaaaag gatgatgatg   3120
aatttgaatt atcttaagat cctggatggt catcgggagc ttgatattag agatgacttt    3180
gtgatggatc tcttcaaagc ttatcatggc gaggcagaag ttccatgggc ctttaaaggc    3240
aaaacatatt tggaaaccac aacagggatg atgcagggaa tactgcatta tacttcctca    3300
ctattacaca ccattcacca agaatacatc cggtccttgt cctttaagat attcaacctg    3360
aaggttgctc ctgagatgag caagggcctg gtttgtgaca tgatgcaagg atcagatgat    3420
agtagtatgc taatcagctt cccagctgat gatgagaagg ttcttaccag atgcaaagtg    3480
gccgcagcta tatgcttccg catgaagaag gagctgggag tgtaccttgc catttacccc    3540
tcagagaagt ccacagcaaa cacagatttt gtgatggagt acaattctga attttatttc    3600
cacacccagc atgttagacc aacgatcagg tggattgcag cttgttgcag cctgccagaa    3660
gtggaaacac tagtagcccg ccaggaagag gcctctaacc taatgacttc agttactgag    3720
ggaggtgggt cattctcctt agctgcaatg attcagcaag ctcagtgcac tctccattac    3780
atgctgatgg gcatgggagt gtctgagcta ttcttagagt ataagaaggc agtgctgaag    3840
tggaatgacc ctggcctggg tttcttcctg cttgacaatc cttatgcgtg cggattggga    3900
ggtttcagat ttaatctctt caaagctatc accagaactg attgcagaa gctatatgct     3960 ttcttcatga agaaggtcaa gggctcagct gctagggact gggcagatga agatgtcacc    4020
atcccagaaa cgtgtagcgt gagcccaggt ggcgctctaa ttcttagctc ctctctaaag    4080
tggggatcta ggaagaagtt tcagaaattg agagaccgtt tgaacatacc agagaactgg    4140
attgaactaa taaatgagaa tccagaggtg ctctatcggg ctcccagaac aggcccagaa    4200
atattgttgc gcattgcaga gaaagtccat agcccaggtg ttgtgtcatc attgtcttct    4260
ggcaatgcag tttgtaaagt catggcctca gctgtatact tcttatcagc aacaattttt    4320
gaggacactg gacgtcctga gttcaacttc ttggaggatt ctaagtacag cttgctacaa    4380
aagatggctg catattctgg cttttcatggt tttaatgata tggagccaga agatatatta    4440
ttcttattcc cgaatattga ggaattagaa tcactggatt ctatagttta caacaaggga    4500
gaaatagaca tcatcccaag agtcaacatc agggatgcaa cccaaaccag ggtcactatc    4560
tttaatgagc agaagaccct ccggacatct ccagagaagt tggtgtcaga caagtggttt    4620
gggactcaga gagtaggat aggcaaaaca accttcctgg ctgaatggga aaagctaaag    4680
aaaattgtaa agtggttgga agacactcca gaagcaactc tagctcacac cccactgaat    4740
```

```
aaccatattc aagttaggaa tttctttgct agaatggaaa gcaagcctag aacagtcaga    4800
ataacaggag ctccagtaaa gaagaggtca ggggttagta agatagctat ggttatccgt    4860
gacaatttct cccggatggg ccatcttcga ggtgtagaag accttgctgg cttcactcgt    4920
agtgtgtcag ctgaaattct caagcacttt ctattctgta tactacaagg tccatacagt    4980
gagagctata agctacagct aatctacaga gtcctaagct cagtgtcaaa cgttgagata    5040
aaggaatcag atggtaagac aaaaaccaac ttgattggaa tccttcagag atttctagat    5100
ggtgatcacg ttgtccccat aattgaagag atgggagccg aacagtggg tggattcatc     5160 aagagacaac aatctaaagt tgtgcagaac aaagtggtct attatggagt tgggatttgg    5220
agaggcttca tggatggata tcaggtccat ctagagatag aaaatgacat aggacagccc    5280
ccaaggctta ggaatgtcac aactaactgt cagagcagcc catgggacct gagtattcca    5340
ataaggcaat gggcagaaga catgggggtc acaaacaacc aggattattc ctctaaatct    5400
agcagagggg ccagatattg gatgcattca ttcaggatgc aaggacctag caagccattt    5460
ggatgcccag tttatattat taagggtgat atgtcagatg tcatcagact gagaaaggag    5520
gaggtggaga tgaaagtacg gggctctact ctcaacttgt acaccaagca ccattctcat    5580
caggacctac acattctatc ttacactgca tcagacaatg atctcagtcc aggcattttc    5640
aagtcaatat cagatgaggg ggtggctcaa gccctgcaat tatttgagag ggagccaagc    5700
aactgctggg tgagatgtga gtctgtagcc ccaaaattta tcagccat ccttgagata      5760 tgtgagggga agagacagat aaggggaatt aacagaacca gactctcaga gattgtgaga    5820
atttgttctg aatcttccct aagatcaaaa gtcggatcta tgttctcatt tgtcgccaat    5880
gtcgaggagg cccatgatgt tgattatgat gcgttaatgg atctaatgat agaggatgcc    5940
aagaacaatg cattcagtca tgttgttgac tgcatagagt tggatgttag tggcccttac    6000
gagatggagt cttttgatac atctgatgtc aatctctttg ggccagccca ttacaaggac    6060
atcagttcat tatctatgat tgctcatccc ttaatggata gtttgttga ttatgctatt      6120 tctaagatgg ggagagcctc agttaggaaa gttctagaaa caggtcggtg ctccagcaaa    6180
gactatgatt tatcaaaggt tctcttcaga actctacaga gaccagaaga aagcattagg    6240
atagatgatc tggaattata tgaggagaca gatgtggcgg atgacatgct aggctaagac    6300
caataagcaa agtcaggctt agatttaggg atactatgct agtattggaa tccatgtggg    6360
ttctgatact agcatagtgc tacaatattg ggcggtcttt gtgt                     6404

<210> SEQ ID NO 4
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 4
aaaaaaggta ccgatatact tgataagcac tag                                 33

<210> SEQ ID NO 5
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 5
aaaaaaagat ctgattagag gttaaggctg                                     30
```

<210> SEQ ID NO 6
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 6
aaaaaaggta ccatggtgag caagggcgag gag					33

<210> SEQ ID NO 7
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 7
aaaaaaagat ctttacttgt acagctcgtc catg					34

<210> SEQ ID NO 8
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 8
aaaaaaggta cctgctgctg catcaacctc aacaaatcca tc				42

<210> SEQ ID NO 9
<211> LENGTH: 49
<212> TYPE: DNA
<213> ORGANISM: Artificial sequence
<220> FEATURE:
<223> OTHER INFORMATION: Synthetic oligonucleotide

<400> SEQUENCE: 9
aaaaaacgtc tcagcagcag cagcagcaat ggtgagcaag ggcgaggag			49

<210> SEQ ID NO 10
<211> LENGTH: 53
<212> TYPE: DNA
<213> ORGANISM: Artificial sequence
<220> FEATURE:
<223> OTHER INFORMATION: Synthetic oligonucleotide

<400> SEQUENCE: 10
aaaaaacgtc tcactgctgc tgctgctgct gcatcaacct caacaaatcc atc		53

<210> SEQ ID NO 11
<211> LENGTH: 4594
<212> TYPE: DNA
<213> ORGANISM: Artificial sequence
<220> FEATURE:
<223> OTHER INFORMATION: Synthetic Plasmid

<400> SEQUENCE: 11
acacaaagct ccctagagat acaaacacta ttacaataat ggacaactat caagagcttg	60 cgatccagtt tgctgctcaa gcagtggacc gcaatgagat tgaacagtgg gtccgagagt	120 ttgcttatca agggtttgat gcccgtagag ttatcgaact cttaaagcag tatggtgggg	180 ctgactggga aaggatgcc aagaaaatga ttgttctggc tctaactcgt ggcaacaagc	240

-continued

```
ccaggaggat gatgatgaaa atgtcgaaag aaggcaaagc aactgtggag gctctcatca        300
acaagtataa gctaaaggaa gggaatcctt cccgggatga gttgactcta tcacgagttg        360
ctgccgccct ggctggctgg acatgccagg ctttggtcgt cttgagtgag tggcttcctg        420
tcactgggac taccatggac ggcctatccc ctgcataccc aaggcatatg atgcacccca        480
gctttgctgg catggtggat ccttctctac caggagacta tctaagggca atattagatg        540
ctcactctct gtatctgctg cagttctccc gggtcatcaa cccaaacctc cgaggtagaa        600
caaaagagga ggttgctgca acgttcacgc agccaatgaa tgcagcagtg aatagcaact        660
ttataagcca tgagaagagg agagaattct tgaaagcctt tggacttgtg gattctaatg        720
ggaagccgtc agctgctgtc atggcagccg ctcaggctta caagacagca gcctaagtgg        780
ctgcccaggg ggttgggggg aaggggagtt ggggttacgg tcgggattgg ggggtggggg        840
gtggggcagc cttaacctct aatcaacctc aacaaatcca tcatcatcac tctcctcctc        900
tgattccatc tcaacatctg ggattggagg aataactgga atccagttgt ttctccccat        960
catgctggga agtgatgagc gcagcatcag gctctcctcc ataagaacaa tgagggctga       1020
gtttggaact acagcattag aaatgtcctc ttttgctgct tgcagaagcc gaacgcactg       1080
tacgtgagca acctcataca tgagatcaaa gcctggcaac aggcacaggt caatccctct       1140
gaggatggcc tcagtcgcta tcatcctgtg taagccaaca aaggagtcct ctagatcatt       1200
ggtgatcttg caactcctca ttgctagagt ggcaatctga tcccttctaa tgtcatcatt       1260
cctatgcact ctagtagagc ttaggtcaaa gaaagccagt gagggttctc caagaggcca       1320
ggatatggct tctttcagat tggggaacct tgtgaaatca ctaagagtca tatggcctat       1380
tagatcaata agtctctgaa aaggcttcgc tggtggaggt gcaacgtttg atgcaaagtc       1440
tccaagtccg actcggtatg ggaattctcc gacattgtag aaatcagaga atcgcaagcg       1500
aacctcgtga ctaggacgat ggtgcatgag aaagacacaa cagggcccaa ccatagaata       1560
aggtatcctg ggaggaccat ctcctctaaa gtactccact gacacaacac gacgaccact       1620
ctgcaaatca acagatatca caggaaagta atccatgata tacttgataa gcactagggg       1680
gtctttgtgt gggtcggcat ggcatctcca cctcctcgcg gtccgacctg gcatccgaa        1740 ggaggacgtc gtccactcgg atggctaagg gagagctcgg atccggctgc taacaaagcc       1800
cgaaaggaag ctgagttggc tgctgccacc gctgagcaat aactagcata acccttggg        1860 gcctctaaac gggtcttgag gggttttttg ctgaaaggag gaactatatc cggatcgaga       1920
tcctctaggt acaagcctaa ttgtgtagca tctggcttac tgaagcagac cctatcatct       1980
ctctcgtaaa ctgccgtcag agtcggtttg gttggacgaa ccttctgagt ttctggtaac       2040
gccgtcccgc acccggaaat ggtcagcgaa ccaatcagca gggtcatcgc tagccagatc       2100
ctctacgccg gacgcatcgt ggccggcatc accggcgcca caggtgcggt tgctggcgcc       2160
tatatcgccg acatcaccga tggggaagat cgggctcgcc acttcgggct catgagcgct       2220
tgtttcggcg tgggtatggt ggcaggcccc gtggccgggg gactgttggg cgccatctcc       2280
ttgcaccatt ccttgcggcg gcggtgctca acggcctcaa cctactactg ggctgcttcc       2340
taatgcagga gtcgcataag ggagagcgtc gatatggtgc actctcagta caatctgctc       2400
tgatgccgca tagttaagcc agccccgaca cccgccaaca cccgctgacg cgccctgacg       2460
ggcttgtctg ctcccggcat ccgcttacag acaagctgtg acaaagggcc tcgtgatacg       2520
cctattttta taggttaatg tcatgataat aatggtttct tagacgtcag gtggcacttt       2580
tcggggaaat gtgcgcggaa cccctatttg tttatttttc taaatacatt caaatatgta       2640
```

```
tccgctcatg agacaataac cctgataaat gcttcaataa tattgaaaaa ggaagagtat    2700
gagtattcaa catttccgtg tcgcccttat tccctttttt gcggcatttt gccttcctgt    2760
ttttgctcac ccagaaacgc tggtgaaagt aaaagatgct gaagatcagt tgggtgcacg    2820
agtgggttac atcgaactgg atctcaacag cggtaagatc cttgagagtt ttcgccccga    2880
agaacgtttt ccaatgatga gcacttttaa agttctgcta tgtggcgcgg tattatcccg    2940
tattgacgcc gggcaagagc aactcggtcg ccgcatacac tattctcaga atgacttggt    3000
tgagtactca ccagtcacag aaaagcatct tacggatggc atgacagtaa gagaattatg    3060
cagtgctgcc ataaccatga gtgataacac tgcggccaac ttacttctga caacgatcgg    3120
aggaccgaag gagctaaccg cttttttgca acatggggg atcatgtaa ctcgccttga    3180 tcgttgggaa ccggagctga atgaagccat accaaacgac gagcgtgaca ccacgatgcc    3240
tgtagcaatg gcaacaacgt tgcgcaaact attaactggc gaactactta ctctagcttc    3300
ccggcaacaa ttaatagact ggatggaggc ggataaagtt gcaggaccac ttctgcgctc    3360
ggcccttccg gctggctggt ttattgctga taaatctgga gccggtgagc gtgggtctcg    3420
cggtatcatt gcagcactgg ggccagatgg taagccctcc cgtatcgtag ttatctacac    3480
gacggggagt caggcaacta tggatgaacg aaatagacag atcgctgaga taggtgcctc    3540
actgattaag cattggtaac tgtcagacca agtttactca tatatacttt agattgattt    3600
aaaacttcat ttttaattta aaaggatcta ggtgaagatc ctttttgata atctcatgac    3660
caaaatccct taacgtgagt tttcgttcca ctgagcgtca gacccgtag aaaagatcaa    3720 aggatcttct tgagatcctt ttttctgcg cgtaatctgc tgcttgcaaa caaaaaaacc    3780
accgctacca gcggtggttt gtttgccgga tcaagagcta ccaactcttt ttccgaaggt    3840
aactggcttc agcagagcgc agataccaaa tactgtcctt ctagtgtagc cgtagttagg    3900
ccaccacttc aagaactctg tagcaccgcc tacatacctc gctctgctaa tcctgttacc    3960
agtggctgct gccagtggcg ataagtcgtg tcttaccggg ttggactcaa gacgatagtt    4020
accggataag gcgcagcggt cgggctgaac ggggggttcg tgcacacagc ccagcttgga    4080
gcgaacgacc tacaccgaac tgagatacct acagcgtgag ctatgagaaa gcgccacgct    4140
tcccgaaggg agaaaggcgg acaggtatcc ggtaagcggc agggtcggaa caggagagcg    4200
cacgagggag cttccagggg gaaacgcctg gtatctttat agtcctgtcg ggtttcgcca    4260
cctctgactt gagcgtcgat ttttgtgatg ctcgtcaggg gggcggagcc tatggaaaaa    4320
cgccagcaac gcggcctttt tacggttcct ggccttttgc tggccttttg ctcacatgtt    4380
ctttcctgcg ttatcccctg attctgtgga taaccgtatt accgcctttg agtgagctga    4440
taccgctcgc cgcagccgaa cgaccgagcg cagcgagtca gtgagcgagg aagcggaaga    4500
gcgcccaata cgcaaaccgc ctctccccgc gcgttggccg attcattaat gcaggggat    4560 ctcgatcccg cgaaattaat acgactcact atag                               4594

<210> SEQ ID NO 12
<211> LENGTH: 6789
<212> TYPE: DNA
<213> ORGANISM: Artificial sequence
<220> FEATURE:
<223> OTHER INFORMATION: Synthetic plasmid

<400> SEQUENCE: 12
acacaaagac ggtgcattaa atgtatgttt tattaacaat tctaatctcg gttctggtgt      60
```

```
gtgaagcggt tattagagtg tctctaagct ccacaagaga agagacctgc tttggtgact    120
ccactaaccc agagatgatt gaaggagctt gggattcact cagagaggag agatgccgg     180 aggagctctc ctgttctata tcaggcataa gagaggttaa gacctcaagc caggagttat    240
acagggcatt aaaagccatc attgctgctg atggcttgaa caacatcacc tgccatggta    300
aggatcctga ggacaagatt tccctcataa agggtcctcc tcacaaaaag cgggtgggga    360
tagttcggtg tgagagacga agagatgcta agcaaatagg gagagaaacc atggcaggga    420
ttgcaatgac agtccttcca gccttagcag tttttgcttt ggcacctgtt gttttgctg     480 aagaccccca tctcagaaac agaccaggga aggggcacaa ctacattgac gggatgactc    540
aggaggatgc cacatgcaaa cctgtgacat atgctggggc atgtagcagt tttgatgtct    600
tgcttgaaaa gggaaaattt cccctttttcc agtcgtatgc tcatcataga actctactag    660
aggcagttca cgacaccatc attgcaaagg ctgatccacc tagctgtgac cttcagagtg    720
ctcatgggaa cccctgcatg aaagagaaac tcgtgatgaa gacacactgt ccaaatgact    780
accagtcagc tcattacctc aacaatgacg ggaaaatggc ttcagtcaag tgccctccta    840
agtatgagct cactgaggac tgcaactttt gtaggcagat gacaggtgct agcctgaaga    900
aggggtctta tcctctccaa gacttgtttt gtcagtcaag tgaggatgat ggatcaaaat    960
taaaaacaaa aatgaaaggg gtctgcgaag tggggttca agcactcaaa aagtgtgatg     1020
gccaactcag cactgcacat gaggttgtgc cctttgcagt gtttaagaac tcaaagaagg    1080
tttatcttga taagcttgac cttaagactg aggagaatct gctaccagac tcatttgtct    1140
gtttcgagca taagggacag tacaaaggaa caatggactc tggtcagact aagagggagc    1200
tcaaaagctt tgatatctct cagtgcccca agattggagg acatggtagt aagaagtgca    1260
ctggggacgc agcattttgc tctgcttatg agtgcactgc tcagtacgcc aatgcctatt    1320
gttcacatgc taatgggtca gggattgtgc agatacaagt atcagggggtc tggaagaagc    1380 ctttatgtgt agggtatgag agagtggttg tgaagagaga actctctgcc aagcccatcc    1440
agagagttga gccttgcaca acttgtataa ccaaatgtga gcctcatgga ttggttgtcc    1500
gatcaacagg gttcaagata tcatcagcag ttgcttgtgc tagcggagtt tgcgtcacag    1560
gatcgcagag tccttccacc gagattacac tcaagtatcc agggatatcc cagtcttctg    1620 gggggggacat aggggttcac atggcacacg atgatcagtc agttagctcc aaaatagtag    1680
ctcactgccc tccccaggac ccgtgtttag tgcatggctg catagtgtgt gctcatggcc    1740
tgataaatta ccagtgtcac actgctctca gtgcctttgt tgttgtgttt gtattcagtt    1800
ctattgcaat aatttgttta gctgttcttt ataggggtgct taagtgcctg aagattgccc    1860
caaggaaagt tctgaatcca ctaatgtgga tcacagcctt catcgatgg atatataaga    1920 agatggttgc cagagtggca gacaacatta atcaagtgaa cagggaaata ggatggatgg    1980
aaggaggtca gttggttcta gggaaccctg cccctattcc tcgtcatgcc ccaatcccac    2040
gttatagcac ataccctgatg ttattattga ttgtctcata tgcatcagca tgttcagaac    2100
tgattcaggc aagctccaga atcaccactt gctctacaga gggtgttaac accaagtgta    2160
gactgtctgg cacagcattg atcagagcag ggtcagttgg ggcagaggct tgtttgatgt    2220 tgaaggggt caaggaagat caaaccaagt tcttaaagat aaaaactgtc tcaagtgagc     2280
tatcatgcag ggagggccag agttattgga ctgggtcctt tagccctaaa tgtttgagct    2340
caaggagatg ccaccttgtc ggggaatgcc atgtgaatag gtgtctgtct tggagggaca    2400
atgaaacttc agcagagttt tcatttgttg gggaaagcac gaccatgcga gagaataagt    2460
```

```
gttttgagca atgtggagga tgggggtgtg ggtgtttcaa tgtgaaccca tcttgcttat    2520
ttgtgcacac gtatctgcag tcagttagaa aagaggccct tagagttttt aactgtatcg    2580
actgggtgca taaactcact ctagagatca cagactttga tggctctgtt tcaacaatag    2640
acttgggagc atcatctagc cgtttcacaa actggggttc agttagcctc tcactggacg    2700
cagagggcat ctcaggctca aatagctttt ctttcattga gagcccaggt aaagggtatg    2760
caattgttga tgagccattc tcagaaattc ctcggcaagg gttcttgggg gagatcaggt    2820
gcaattcaga gtcctcagtc ctgagtgctc atgaatcatg ccttagggca ccaaacctta    2880
tctcatacaa gcccatgata gatcaattgg agtgcacaac aaatctgatt gatcccttttg    2940 ttgtctttga gaggggttct ctgccacaga caaggaatga taaaacccttt gcagcttcaa    3000 aaggaaatag aggtgttcaa gctttctcta agggctctgt acaagctgat ctaactctga    3060
tgtttgacaa ttttgaggtg gactttgtgg agcagccgt atcttgtgat gccgccttct     3120
taaatttgac aggttgctat tcttgcaatg caggggccag ggtctgcctg tctatcacat    3180
ccacaggaac tggatctctc tctgcccaca ataaggatgg gtctctgcat atagtccttc    3240
catcagagaa tggaacaaaa gaccagtgtc agatactaca cttcactgtg cctgaagtag    3300
aggaggagtt tatgtactct tgtgatggag atgagcggcc tctgttggtg aaggggaccc    3360
tgatagccat tgatccatttt gatgataggc gggaagcagg gggggaatca acagttgtga    3420
atccaaaatc tggatcttgg aatttctttg actggttttc tggactcatg agttggtttg    3480
gagggcctct taaaactata ctcctcattt gcctgtatgt tgcattatca attgggctct    3540
ttttcctcct tatatatctt ggaagaacag gcctctctaa aatgtggctt gctgccacta    3600
agaaggcctc atagatcagt acgtgtaaaa gcaatatgtt gaaataagta gacacaagca    3660
aacctaatta tgtaagtgtt gtacagatag gtcaaattat tggaatatcc aagcttagaa    3720
acttatgcaa taatacttta gatgtaagct tagttgtaat ttggggtggt ggggtgaggc    3780
agcagcagtc tcaagtgctt tgtgaatattc tagttggcgt aatcgtctttt tgccagatta    3840 gctgggaatt aaactaactc tttgaagttg caccggtctt tgtgtgggtc ggcatggcat    3900
ctccacctcc tcgcggtccg acctgggcat ccgaaggagg acgtcgtcca ctcggatggc    3960
taagggagag ctcggatccg gctgctaaca aagcccgaaa ggaagctgag ttggctgctg    4020
ccaccgctga gcaataacta gcataacccc ttggggcctc taaacgggtc ttgaggggtt    4080
ttttgctgaa aggaggaact atatccggat cgagatcctc taggtacaag cctaattgtg    4140
tagcatctgg cttactgaag cagaccctat catctctctc gtaaactgcc gtcagagtcg    4200
gtttggttgg acgaaccttc tgagtttctg gtaacgccgt cccgcacccg gaaatggtca    4260
gcgaaccaat cagcagggtc atcgctagcc agatcctcta cgccggacgc atcgtggccg    4320
gcatcaccgg cgccacaggt gcggttgctg gcgcctatat cgccgacatc accgatgggg    4380
aagatcgggc tcgccacttc gggctcatga gcgcttgttt cggcgtgggt atggtggcag    4440
gccccgtggc cggggggactg ttgggcgcca tctccttgca ccattccttg cggcggcggt    4500
gctcaacggc ctcaacctac tactgggctg cttcctaatg caggagtcgc ataagggaga    4560
gcgtcgatat ggtgcactct cagtacaatc tgctctgatg ccgcatagtt aagccagccc    4620
cgacacccgc caacacccgc tgacgcgccc tgacgggctt gtctgctccc ggcatccgct    4680
tacagacaag ctgtgacaaa gggcctcgtg atacgcctat ttttataggt taatgtcatg    4740
ataataatgg tttcttagac gtcaggtggc acttttcggg gaaatgtgcg cggaacccct    4800
```

-continued

```
atttgtttat ttttctaaat acattcaaat atgtatccgc tcatgagaca ataaccctga    4860
taaatgcttc aataatattg aaaaggaag agtatgagta ttcaacattt ccgtgtcgcc     4920
cttattccct tttttgcggc attttgcctt cctgttttg ctcacccaga aacgctggtg    4980
aaagtaaaag atgctgaaga tcagttgggt gcacgagtgg gttacatcga actggatctc    5040
aacagcggta agatccttga gagttttcgc cccgaagaac gttttccaat gatgagcact    5100
tttaaagttc tgctatgtgg cgcggtatta tcccgtattg acgccgggca agagcaactc    5160
ggtcgccgca tacactattc tcagaatgac ttggttgagt actcaccagt cacagaaaag    5220
catcttacgg atggcatgac agtaagagaa ttatgcagtg ctgccataac catgagtgat    5280
aacactgcgg ccaacttact tctgacaacg atcggaggac cgaaggagct aaccgctttt    5340
ttgcacaaca tgggggatca tgtaactcgc cttgatcgtt gggaaccgga gctgaatgaa    5400
gccataccaa acgacgagcg tgacaccacg atgcctgtag caatggcaac aacgttgcgc    5460
aaactattaa ctggcgaact acttactcta gcttcccggc aacaattaat agactggatg    5520
gaggcggata aagttgcagg accacttctg cgctcggccc ttccggctgg ctggtttatt    5580
gctgataaat ctggagccgg tgagcgtggg tctcgcggta tcattgcagc actggggcca    5640
gatggtaagc cctcccgtat cgtagttatc tacacgacgg ggagtcaggc aactatggat    5700
gaacgaaata gacagatcgc tgagataggt gcctcactga ttaagcattg gtaactgtca    5760
gaccaagttt actcatatat actttagatt gatttaaaac ttcatttta atttaaaagg    5820
atctaggtga agatcctttt tgataatctc atgaccaaaa tcccttaacg tgagttttcg    5880
ttccactgag cgtcagaccc cgtagaaaag atcaaaggat cttcttgaga tcctttttt     5940
ctgcgcgtaa tctgctgctt gcaaacaaaa aaaccaccgc taccagcggt ggtttgtttg    6000
ccggatcaag agctaccaac tcttttccg aaggtaactg gcttcagcag agcgcagata    6060
ccaaatactg tccttctagt gtagccgtag ttaggccacc acttcaagaa ctctgtagca    6120
ccgcctacat acctcgctct gctaatcctg ttaccagtgg ctgctgccag tggcgataag    6180
tcgtgtctta ccgggttgga ctcaagacga tagttaccgg ataaggcgca gcggtcgggc    6240
tgaacggggg gttcgtgcac acagcccagc ttggagcgaa cgacctacac cgaactgaga    6300
tacctacagc gtgagctatg agaaagcgcc acgcttcccg aagggagaaa ggcggacagg    6360
tatccggtaa gcggcagggt cggaacagga gagcgcacga gggagcttcc agggggaaac    6420
gcctggtatc tttatagtcc tgtcgggttt cgccacctct gacttgagcg tcgatttttg    6480
tgatgctcgt caggggggcg gagcctatgg aaaaacgcca gcaacgcggc ctttttacgg    6540
ttcctggcct tttgctggcc ttttgctcac atgttctttc ctgcgttatc ccctgattct    6600
gtggataacc gtattaccgc ctttgagtga gctgataccg ctcgccgcag ccgaacgacc    6660
gagcgcagcg agtcagtgag cgaggaagcg gaagagcgcc caatacgcaa accgcctctc    6720
cccgcgcgtt ggccgattca ttaatgcagg gggatctcga tcccgcgaaa ttaatacgac    6780
tcactatag                                                            6789
```

<210> SEQ ID NO 13
<211> LENGTH: 9575
<212> TYPE: DNA
<213> ORGANISM: Artificial sequence
<220> FEATURE:
<223> OTHER INFORMATION: Synthetic plasmid

<400> SEQUENCE: 13

```
acacaaaggc gcccaatcat ggattctata ttatcaaaac agctggttga caagactggt      60
```

```
tttgttagag tgccaatcaa gcatttgac tgtacaatgc taactctggc acttccaaca      120
tttgatgttt ccaagatggt agatagaatt accatagact tcaatctgga tgatatacaa      180
ggagcatctg aaataggctc aactttgcta ccctccatgt cgatagatgt ggaagatatg      240
gccaattttg ttcacgattt caccttggc cacttagctg acaagactga cagactgtta       300
atgcgtgagt ttcccatgat gaatgacggg tttgatcatt tgagccctga catgatcatt      360
aaaactacat ctggcatgta caacatcgtt gagttcacca cctttagggg agatgaaaga      420
ggtgcattcc aggctgccat gactaaactc gctaagtatg aggttccttg tgagaacaga      480
tctcagggca ggactgttgt tctttatgtt gttagtgctt atcggcatgg tgtatggtct      540
aatctggagc tagaggactc tgaagcagag gagatggttt ataggtacag acttgctctt      600
agtgtgatgg atgagctaag gaccttgttc ccagaactgt catccacaga tgaggaacta      660
gggaagactg agagagagtt gctagccatg gtctcctcca tccaaataaa ttggtcagtc      720
acagaatctg tgtttccacc cttcagcaga gaaatgtttg acaggtttag atcctcccct      780
cccgattcag agtatatcac gaggatagtg agcagatgcc tcataaattc tcaagagaaa      840
ctcatcaata gttccttctt tgctgaaggg aatgataagg ctctgagatt ttcaaaaaac      900
gctgaagagt gttccttggc agtagagaga gccttaaatc agtatagagc agaagacaac      960
cttagggacc tcaatgacca caagtcaact attcagctgc ctccctggct gtcctatcat     1020
gatgtcgatg gcaaagatct gtgccctctt cagggattag atgtgagagg ggaccatccc     1080
atgtgcaact tgtggaggga agtggtcacc tctgcaaacc tagaggagat tgagaggatg     1140
cacgatgatg cagcagcaga acttgagttt gctctttcgg gagtaaagga caggccagat     1200
gagagaaaca gataccatag agtccaccta aatatgggct cagatgatag tgtctacata     1260
gctgctttag gagttaatgg aaagaagcat aaagcagaca ctttagtgca acaaatgaga     1320
gacaggagta aacagccttt ctccccagac cacgatgtgg atcacatatc tgaatttctc     1380
tctgcatgct ctagtgactt gtgggcaaca gatgaggacc tgtacaaccc tctctcttgt     1440
gataaagagc ttagattggc agcccagagg attcatcagc catccttgtc agaaagggt      1500 ttcaatgaga tcataacaga gcactacaaa ttcatgggaa gtaggatagg ttcatggtgc     1560
caaatggtca gcttgatagg agctgagcta tcagcttctg ttaaacaaca tgtcaagcct     1620
aactactttg tgattaaacg actactaggt tctgggattt tcttgctaat caagcccact     1680
tccagcaaaa gccatatatt tgtgtctttt gcaattaagc gctcttgctg ggcctttgat     1740
ctctccactt ccagggtttt caagccctac atagatgctg gggatctgtt agttactgac     1800
tttgtttctt ataagctaag caagcttacc aacctctgca gtgcgtttc attaatggag       1860 tcctccttct cattctgggc agaagcattt ggcattccaa gctggaactt tgttggtgac     1920
ttgttcaggt cttcagactc tgcagcaatg gatgcctcat acatgggcaa actttctta      1980 ttaaccctt tggaagacaa agcagcaact gaagagttac agactattgc aagatatata     2040
atcatggagg gctttgtctc gccccagaa atcccaaaac ctcacaagat gacctctaag      2100
tttcctaagg ttctcaggtc agagctgcag gtttacttat taaactgctt atgcagaact     2160
atccagagaa tagcaggtga gcccttcatt cttaagaaga aggatgggtc tatatcctgg     2220
ggtggcatgt tcaatccttt ttcagggcgt ccactgcttg atatgcaacc actcatcagc     2280
tgttgttaca atggttactt taaaaataaa gaagaagaga ctgagccttc gtcccttttct    2340 gggatgtata agaaaatcat agaacttgag caccttagac cacagtcaga tgccttcttg     2400
```

```
ggttacaaag atccagaact tcccagaatg catgagttca gtgtttccta cttgaaggag    2460
gcttgcaatc atgctaagct agtcttgagg agcctctatg gacagaattt catggagcag    2520
atagacaacc agattattcg agagctcagt gggttgactc tagaaaggtt ggccacactt    2580
aaggccacaa gcaactttaa tgagaattgg tatgtctata aggatgtagc agacaaaaac    2640
tacacaaggg ataaattatt agtgaagatg tcaaatatg cctctgaggg aaagagccta    2700
gctatccaga agtttgagga ttgtatgagg cagatagagt cacaaggatg catgcatatt    2760
tgtttgttta agaaacaaca gcatggaggt ctgagagaga tctatgtgat gggtgcagag    2820
gaaagaattg ttcaatcggt ggtggagaca atagccaggt ccatagggaa gttctttgct    2880
tctgataccc tctgtaaccc ccccaataaa gtgaaaattc ctgagacaca tggcatcagg    2940
gcccggaagc aatgtaaggg gcctgtgtgg acttgtgcaa catcagatga tgcaaggaag    3000
tggaaccaag gccattttgt tacaaagttt gccctcatgc tgtgtgagtt cacctctcct    3060
aaatggtggc cgctgatcat taggggatgc tcaatgttta ccaggaaaag gatgatgatg    3120
aatttgaatt atcttaagat cctggatggt catcgggagc ttgatattag agatgacttt    3180
gtgatggatc tcttcaaagc ttatcatggc gaggcagaag ttccatgggc ctttaaaggc    3240
aaaacatatt tggaaaccac aacagggatg atgcaggaa tactgcatta tacttcctca    3300
ctattacaca ccattcacca agaatacatc cggtccttgt cctttaagat attcaacctg    3360
aaggttgctc ctgagatgag caagggcctg gtttgtgaca tgatgcaagg atcagatgat    3420
agtagtatgc taatcagctt cccagctgat gatgagaagg ttcttaccag atgcaaagtg    3480
gccgcagcta tatgcttccg catgaagaag gagctgggag tgtaccttgc catttacccc    3540
tcagagaagt ccacagcaaa cacagatttt gtgatggagt acaattctga atttatttc    3600 cacacccagc atgttagacc aacgatcagg tggattgcag cttgttgcag cctgccagaa    3660
gtggaaacac tagtagcccg ccaggaagag gcctctaacc taatgacttc agttactgag    3720
ggaggtgggt cattctcctt agctgcaatg attcagcaag ctcagtgcac tctccattac    3780
atgctgatgg gcatgggagt gtctgagcta ttcttagagt ataagaaggc agtgctgaag    3840
tggaatgacc ctggcctggg tttcttcctg cttgacaatc cttatgcgtg cggattggga    3900
ggtttcagat ttaatctctt caaagctatc accagaactg atttgcagaa gctatatgct    3960
ttcttcatga agaaggtcaa gggctcagct gctagggact gggcagatga agatgtcacc    4020
atcccagaaa cgtgtagcgt gagcccaggt ggcgctctaa ttcttagctc ctctctaaag    4080
tggggatcta ggaagaagtt tcagaaattg agagaccgtt tgaacatacc agagaactgg    4140
attgaactaa taaatgagaa tccagaggtg ctctatcggg ctcccagaac aggcccagaa    4200
atattgttgc gcattgcaga gaaagtccat agcccaggtg ttgtgtcatc attgtcttct    4260
ggcaatgcag tttgtaaagt catggcctca gctgtatact tcttatcagc aacaatttt    4320 gaggacactg gacgtcctga gttcaacttc ttggaggatt ctaagtacag cttgctacaa    4380
aagatggctg catattctgg cttttcatggt tttaatgata tggagccaga agatatatta    4440
ttcttattcc gaatattga ggaattagaa tcactggatt ctatagttta caacaaggga    4500
gaaatagaca tcatcccaag agtcaacatc agggatgcaa cccaaaccag ggtcactatc    4560
tttaatgagc agaagaccct ccggacatct ccagagaagt tggtgtcaga caagtggttt    4620
gggactcaga gagtaggat aggcaaaaca accttcctgg ctgaatggga aaagctaaag    4680
aaaattgtaa agtggttgga agacactcca gaagcaactc tagctcacac cccactgaat    4740
aaccatattc aagttaggaa tttctttgct agaatggaaa gcaagcctag aacagtcaga    4800
```

```
ataacaggag ctccagtaaa gaagaggtca ggggttagta agatagctat ggttatccgt    4860
gacaatttct cccggatggg ccatcttcga ggtgtagaag accttgctgg cttcactcgt    4920
agtgtgtcag ctgaaattct caagcacttt ctattctgta tactacaagg tccatacagt    4980
gagagctata agctacagct aatctacaga gtcctaagct cagtgtcaaa cgttgagata    5040
aaggaatcag atggtaagac aaaaaccaac ttgattggaa tccttcagag atttctagat    5100
ggtgatcacg ttgtccccat aattgaagag atgggagccg aacagtggg tggattcatc    5160 aagagacaac aatctaaagt tgtgcagaac aaagtggtct attatggagt tgggatttgg    5220
agaggcttca tggatggata tcaggtccat ctagagatag aaaatgacat aggacagccc    5280
ccaaggctta ggaatgtcac aactaactgt cagagcagcc catgggacct gagtattcca    5340
ataaggcaat gggcagaaga catgggggtc acaaacaacc aggattattc ctctaaatct    5400
agcagagggg ccagatattg gatgcattca ttcaggatgc aaggacctag caagccattt    5460
ggatgcccag tttatattat taagggtgat atgtcagatg tcatcagact gagaaaggag    5520
gaggtggaga tgaaagtacg gggctctact ctcaacttgt acaccaagca ccattctcat    5580
caggacctac acattctatc ttacactgca tcagacaatg atctcagtcc aggcattttc    5640
aagtcaatat cagatgaggg ggtggctcaa gccctgcaat tatttgagag ggagccaagc    5700
aactgctggg tgatgtga gtctgtagcc ccaaaattta tatcagccat ccttgagata    5760
tgtgagggga agagacagat aagggggaatt aacagaacca gactctcaga gattgtgaga    5820
atttgttctg aatcttccct aagatcaaaa gtcggatcta tgttctcatt tgtcgccaat    5880
gtcgaggagg cccatgatgt tgattatgat gcgttaatgg atctaatgat agaggatgcc    5940
aagaacaatg cattcagtca tgttgttgac tgcatagagt tggatgttag tggcccttac    6000
gagatggagt cttttgatac atctgatgtc aatctctttg gccagcccca ttacaaggac    6060
atcagttcat tatctatgat tgctcatccc ttaatggata agtttgttga ttatgctatt    6120
tctaagatgg ggagagcctc agttaggaaa gttctagaaa caggtcggtg ctccagcaaa    6180
gactatgatt tatcaaaggt tctcttcaga actctacaga gaccagaaga aagcattagg    6240
atagatgatc tggaattata tgaggagaca gatgtggcgg atgacatgct aggctaagac    6300
caataagcaa agtcaggctt agatttaggg atactatgct agtattggaa tccatgtggg    6360
ttctgatact agcatagtgc tacaatattg ggcggtcttt gtgtgggtcg gcatggcatc    6420
tccacctcct cgcggtccga cctgggcatc cgaaggagga cgtcgtccac tcggatggct    6480
aagggagcaa gcttagcggt caccgctgag caataactag cataacccct tggggcctct    6540
aaacgggtct tgaggggttt tttaagccga attcgtaatc atgtcatagc tgtttcctgt    6600
gtgaaattgt tatccgctca caattccaca acaatacga gccggaagca taaagtgtaa    6660
agcctggggt gcctaatgag tgagctaact cacattaatt gcgttgcgct cactgcccgc    6720
tttccagtcg ggaaacctgt cgtgccagct gcattaatga atcggccaac gcgcggggag    6780
aggcggtttg cgtattgggc gctcttccgc ttcctcgctc actgactcgc tgcgctcggt    6840
cgttcggctg cggcgagcgg tatcagctca ctcaaaggcg gtaatacggt tatccacaga    6900
atcaggggat aacgcaggaa agaacatgtg agcaaaaggc cagcaaaagg ccaggaaccg    6960
taaaaaggcc gcgttgctgg cgtttttcca taggctccgc cccccctgacg agcatcacaa    7020 aaatcgacgc tcaagtcaga ggtggcgaaa cccgacagga ctataaagat accaggcgtt    7080
tccccctgga agctccctcg tgcgctctcc tgttccgacc ctgccgctta ccggatacct    7140
```

```
gtccgccttt ctcccttcgg gaagcgtggc gctttctcat agctcacgct gtaggtatct   7200
cagttcggtg taggtcgttc gctccaagct gggctgtgtg cacgaacccc ccgttcagcc   7260
cgaccgctgc gccttatccg gtaactatcg tcttgagtcc aacccggtaa gacacgactt   7320
atcgccactg gcagcagcca ctggtaacag gattagcaga gcgaggtatg taggcggtgc   7380
tacagagttc ttgaagtggt ggcctaacta cggctacact agaagaacag tatttggtat   7440
ctgcgctctg ctgaagccag ttaccttcgg aaaagagtt ggtagctctt gatccggcaa   7500
acaaaccacc gctggtagcg gtggttttt tgtttgcaag cagcagatta cgcgcagaaa   7560
aaaaggatct caagaagatc ctttgatctt ttctacgggg tctgacgctc agtggaacga   7620
aaactcacgt taagggattt tggtcatgag attatcaaaa aggatcttca cctagatcct   7680
tttaaattaa aaatgaagtt ttaaatcaat ctaaagtata tatgagtaaa cttggtctga   7740
cagttaccaa tgcttaatca gtgaggcacc tatctcagcg atctgtctat ttcgttcatc   7800
catagttgcc tgactccccg tcgtgtagat aactacgata cgggagggct taccatctgg   7860
ccccagtgct gcaatgatac cgcgagaccc acgctcaccg gctccagatt tatcagcaat   7920
aaaccagcca gccggaaggg ccgagcgcag aagtggtcct gcaactttat ccgcctccat   7980
ccagtctatt aattgttgcc gggaagctag agtaagtagt tcgccagtta atagtttgcg   8040
caacgttgtt gccattgcta caggcatcgt ggtgtcacgc tcgtcgtttg gtatggcttc   8100
attcagctcc ggttcccaac gatcaaggcg agttacatga tcccccatgt tgtgcaaaaa   8160
agcggttagc tccttcggtc ctccgatcgt tgtcagaagt aagttggccg cagtgttatc   8220
actcatggtt atggcagcac tgcataattc tcttactgtc atgccatccg taagatgctt   8280
ttctgtgact ggtgagtact caaccaagtc attctgagaa tagtgtatgc ggcgaccgag   8340
ttgctcttgc ccggcgtcaa tacgggataa taccgcgcca catagcagaa ctttaaaagt   8400
gctcatcatt ggaaaacgtt cttcggggcg aaaactctca aggatcttac cgctgttgag   8460
atccagttcg atgtaaccca ctcgtgcacc caactgatct tcagcatctt ttactttcac   8520
cagcgtttct gggtgagcaa aaacaggaag gcaaaatgcc gcaaaaaagg gaataagggc   8580
gacacggaaa tgttgaatac tcatactctt cctttttcaa tattattgaa gcatttatca   8640
gggttattgt ctcatgagcg gatacatatt tgaatgtatt tagaaaaata aacaaatagg   8700
ggttccgcgc acatttcccc gaaaagtgcc acctgacgtc taagaaacca ttattatcat   8760
gacattaacc tataaaaata ggcgtatcac gaggcccttt cgtctcgcgc gtttcggtga   8820
tgacggtgaa aacctctgac acatgcagct cccggagacg gtcacagctt gtctgtaagc   8880
ggatgccggg agcagacaag cccgtcaggg cgcgtcagcg ggtgttggcg ggtgtcgggg   8940
ctggcttaac tatgcggcat cagagcagat tgtactgaga gtgcaccatt cgacgctctc   9000
ccttatgcga ctcctgcatt aggaagcagc ccagtagtag gttgaggccg ttgagcaccg   9060
ccgccgcaag gaatggtgca tgcaaggaga tggcgcccaa cagtcccccg gccacggggc   9120
ctgccaccat acccacgccg aaacaagcgc tcatgagccc gaagtggcga gcccgatctt   9180
ccccatcggt gatgtcggcg atataggcgc cagcaaccgc acctgtggcg ccggtgatgc   9240
cggccacgat gcgtccggcg tagaggatct ggctagcgat gaccctgctg attggttcgc   9300
tgaccatttc cgggtgcggg acggcgttac cagaaactca gaaggttcgt ccaaccaaac   9360
cgactctgac ggcagtttac gagagagatg atagggtctg cttcagtaag ccagatgcta   9420
cacaattagg cttgtacata ttgtcgttag aacgcggcta caattaatac ataaccttat   9480
gtatcataca catacgattt aggtgacact atagaataca agctagcttg gctgcaggt   9540
```
cgacttctag aggatcctaa tacgactcac tatag 9575

<210> SEQ ID NO 14
<211> LENGTH: 4534
<212> TYPE: DNA
<213> ORGANISM: Artificial sequence
<220> FEATURE:
<223> OTHER INFORMATION: Synthetic plasmid

<400> SEQUENCE: 14

| | |
|---|---|
| acacaaagct ccctagagat acaaacacta ttacaataat ggacaactat caagagcttg | 60 |
| cgatccagtt tgctgctcaa gcagtggacc gcaatgagat tgaacagtgg gtccgagagt | 120 |
| ttgcttatca agggtttgat gcccgtagag ttatcgaact cttaaagcag tatggtgggg | 180 |
| ctgactggga gaaggatgcc aagaaaatga ttgttctggc tctaactcgt ggcaacaagc | 240 |
| ccaggaggat gatgatgaaa atgtcgaaag aaggcaaagc aactgtggag gctctcatca | 300 |
| acaagtataa gctaaaggaa gggaatcctt cccgggatga gttgactcta tcacgagttg | 360 |
| ctgccgccct ggctggctgg acatgccagg cttttggtcgt cttgagtgag tggcttcctg | 420 |
| tcactgggac taccatggac ggcctatccc ctgcataccc aaggcatatg atgcacccca | 480 |
| gctttgctgg catggtggat ccttctctac caggagacta tctaagggca atattagatg | 540 |
| ctcactctct gtatctgctg cagttctccc gggtcatcaa cccaaacctc cgaggtagaa | 600 |
| caaaagagga ggttgctgca acgttcacgc agccaatgaa tgcagcagtg aatagcaact | 660 |
| ttataagcca tgagaagagg agagaattct tgaaagcctt tggacttgtg gattctaatg | 720 |
| ggaagccgtc agctgctgtc atggcagccg ctcaggctta aagacagca gcctaagtgg | 780 |
| ctgcccaggg ggttgggggg aaggggagtt ggggttacgg tcgggattgg ggggtggggg | 840 |
| gtggggcagc cttaacctct aatcagatct ttacttgtac agctcgtcca tgccgagagt | 900 |
| gatcccggcg gcggtcacga actccagcag gaccatgtga tcgcgcttct cgttggggtc | 960 |
| tttgctcagg gcggactggg tgctcaggta gtggttgtcg ggcagcagca cggggccgtc | 1020 |
| gccgatgggg gtgttctgct ggtagtggtc ggcgagctgc acgctgccgt cctcgatgtt | 1080 |
| gtggcggatc ttgaagttca ccttgatgcc gttcttctgc ttgtcggcca tgatatagac | 1140 |
| gttgtggctg ttgtagttgt actccagctt gtgccccagg atgttgccgt cctccttgaa | 1200 |
| gtcgatgccc ttcagctcga tgcggttcac cagggtgtcg ccctcgaact tcacctcggc | 1260 |
| gcgggtcttg tagttgccgt cgtccttgaa gaagatggtg cgctcctgga cgtagccttc | 1320 |
| gggcatggcg gacttgaaga agtcgtgctg cttcatgtgg tcggggtagc ggctgaagca | 1380 |
| ctgcacgccg taggtcaggg tggtcacgag ggtgggccag ggcacgggca gcttgccggt | 1440 |
| ggtgcagatg aacttcaggg tcagcttgcc gtaggtggca tcgccctcgc cctcgccgga | 1500 |
| cacgctgaac ttgtggccgt ttacgtcgcc gtccagctcg accaggatgg gcaccacccc | 1560 |
| ggtgaacagc tcctcgccct tgctcaccat ggtaccgata tacttgataa gcactagggg | 1620 |
| gtctttgtgt gggtcggcat ggcatctcca cctcctcgcg gtccgacctg gcatccgaa | 1680 |
| ggaggacgtc gtccactcgg atggctaagg gagagctcgg atccggctgc taacaaagcc | 1740 |
| cgaaaggaag ctgagttggc tgctgccacc gctgagcaat aactagcata accccttggg | 1800 |
| gcctctaaac gggtcttgag gggttttttg ctgaaaggag gaactatatc cggatcgaga | 1860 |
| tcctctaggt acaagcctaa ttgtgtagca tctggcttac tgaagcagac cctatcatct | 1920 |
| ctctcgtaaa ctgccgtcag agtcggtttg gttggacgaa ccttctgagt ttctggtaac | 1980 |

```
gccgtcccgc acccggaaat ggtcagcgaa ccaatcagca gggtcatcgc tagccagatc    2040
ctctacgccg gacgcatcgt ggccggcatc accggcgcca caggtgcggt tgctggcgcc    2100
tatatcgccg acatcaccga tggggaagat cgggctcgcc acttcgggct catgagcgct    2160
tgtttcggcg tgggtatggt ggcaggcccc gtggccgggg gactgttggg cgccatctcc    2220
ttgcaccatt ccttgcggcg gcggtgctca acggcctcaa cctactactg ggctgcttcc    2280
taatgcagga gtcgcataag ggagagcgtc gatatggtgc actctcagta caatctgctc    2340
tgatgccgca tagttaagcc agccccgaca cccgccaaca cccgctgacg cgccctgacg    2400
ggcttgtctg ctcccggcat ccgcttacag acaagctgtg acaaagggcc tcgtgatacg    2460 cctatttta taggttaatg tcatgataat aatggtttct tagacgtcag gtggcacttt    2520
tcggggaaat gtgcgcggaa cccctatttg tttatttttc taaatacatt caaatatgta    2580
tccgctcatg agacaataac cctgataaat gcttcaataa tattgaaaaa ggaagagtat    2640
gagtattcaa catttccgtg tcgcccttat tccctttttt gcggcatttt gccttcctgt    2700
ttttgctcac ccagaaacgc tggtgaaagt aaaagatgct gaagatcagt tgggtgcacg    2760
agtgggttac atcgaactgg atctcaacag cggtaagatc cttgagagtt ttcgccccga    2820
agaacgtttt ccaatgatga gcacttttaa agttctgcta tgtggcgcgg tattatcccg    2880
tattgacgcc gggcaagagc aactcggtcg ccgcatacac tattctcaga atgacttggt    2940
tgagtactca ccagtcacag aaaagcatct tacggatggc atgacagtaa gagaattatg    3000
cagtgctgcc ataaccatga gtgataacac tgcggccaac ttacttctga caacgatcgg    3060
aggaccgaag gagctaaccg cttttttgca caacatgggg gatcatgtaa ctcgccttga    3120
tcgttgggaa ccggagctga atgaagccat accaaacgac gagcgtgaca ccacgatgcc    3180
tgtagcaatg gcaacaacgt tgcgcaaact attaactggc gaactactta ctctagcttc    3240
ccggcaacaa ttaatagact ggatggaggc ggataaagtt gcaggaccac ttctgcgctc    3300
ggcccttccg ctggctggtt tattgctga taaatctgga gccggtgagc gtgggtctcg    3360
cggtatcatt gcagcactgg ggccagatgg taagccctcc cgtatcgtag ttatctacac    3420
gacggggagt caggcaacta tggatgaacg aaatagacag atcgctgaga taggtgcctc    3480
actgattaag cattggtaac tgtcagacca agtttactca tatatacttt agattgattt    3540
aaaacttcat ttttaattta aaaggatcta ggtgaagatc ctttttgata atctcatgac    3600
caaaatccct aacgtgagt tttcgttcca ctgagcgtca gaccccgtag aaaagatcaa    3660
aggatcttct tgagatcctt ttttctgcg cgtaatctgc tgcttgcaaa caaaaaaacc    3720
accgctacca gcggtggttt gtttgccgga tcaagagcta ccaactcttt ttccgaaggt    3780
aactggcttc agcagagcgc agataccaaa tactgtcctt ctagtgtagc cgtagttagg    3840
ccaccacttc aagaactctg tagcaccgcc tacatacctc gctctgctaa tcctgttacc    3900
agtggctgct gccagtggcg ataagtcgtg tcttaccggg ttggactcaa gacgatagtt    3960
accggataag gcgcagcggt cgggctgaac ggggggttcg tgcacacagc ccagcttgga    4020
gcgaacgacc tacaccgaac tgagatacct acagcgtgag ctatgagaaa gcgccacgct    4080
tcccgaaggg agaaaggcgg acaggtatcc ggtaagcggc agggtcggaa caggagagcg    4140
cacgagggag cttccagggg gaaacgcctg gtatctttat agtcctgtcg gtttcgccca    4200
cctctgactt gagcgtcgat ttttgtgatg ctcgtcaggg gggcggagcc tatggaaaaa    4260
cgccagcaac gcggcctttt tacgttcct ggccttttgc tggccttttg ctcacatgtt    4320
ctttcctgcg ttatcccctg attctgtgga taaccgtatt accgcctttg agtgagctga    4380
```

```
taccgctcgc cgcagccgaa cgaccgagcg cagcgagtca gtgagcgagg aagcggaaga    4440
gcgcccaata cgcaaaccgc ctctccccgc gcgttggccg attcattaat gcaggggat    4500 ctcgatcccg cgaaattaat acgactcact atag                              4534

<210> SEQ ID NO 15
<211> LENGTH: 6652
<212> TYPE: DNA
<213> ORGANISM: Artificial sequence
<220> FEATURE:
<223> OTHER INFORMATION: Synthetic plasmid

<400> SEQUENCE: 15
acacaaagac ggtgcattaa accatggcag ggattgcaat gacagtcctt ccagccttag      60 cagttttttgc tttggcacct gttgttttttg ctgaagaccc ccatctcaga aacagaccag    120
ggaaggggca caactacatt gacgggatga ctcaggagga tgccacatgc aaacctgtga    180
catatgctgg ggcatgtagc agttttgatg tcttgcttga aagggaaaa tttccccttt     240 tccagtcgta tgctcatcat agaactctac tagaggcagt tcacgacacc atcattgcaa    300
aggctgatcc acctagctgt gaccttcaga gtgctcatgg gaaccccctgc atgaaagaga    360 aactcgtgat gaagacacac tgtccaaatg actaccagtc agctcattac ctcaacaatg    420
acgggaaaat ggcttcagtc aagtgccctc ctaagtatga gctcactgag gactgcaact    480
tttgtaggca gatgacaggt gctagcctga agaaggggtc ttatcctctc caagacttgt    540
tttgtcagtc aagtgaggat gatggatcaa aattaaaaac aaaaatgaaa gggtctgcg    600 aagtgggggt tcaagcactc aaaaagtgtg atggccaact cagcactgca catgaggttg    660 tgcccttttgc agtgtttaag aactcaaaga aggtttatct tgataagctt gaccttaaga    720
ctgaggagaa tctgctacca gactcatttg tctgtttcga gcataaggga cagtacaaag    780
gaacaatgga ctctggtcag actaagaggg agctcaaaag ctttgatatc tctcagtgcc    840
ccaagattgg aggacatggt agtaagaagt gcactgggga cgcagcattt tgctctgctt    900
atgagtgcac tgctcagtac gccaatgcct attgttcaca tgctaatggg tcagggattg    960
tgcagataca agtatcaggg gtctggaaga agcctttatg tgtaggggtat gagagagtgg   1020 ttgtgaagag agaactctct gccaagccca tccagagagt tgagccttgc acaacttgta    1080
taaccaaatg tgagcctcat ggattggttg tccgatcaac agggttcaag atatcatcag   1140
cagttgcttg tgctagcgga gtttgcgtca caggatcgca gagtccttcc accgagatta   1200
cactcaagta tccagggata tcccagtctt ctgggggga catagggggtt cacatggcac    1260 acgatgatca gtcagttagc tccaaaatag tagctcactg ccctcccag acccgtgtt     1320 tagtgcatgg ctgcatagtg tgtgctcatg gcctgataaa ttaccagtgt cacactgctc    1380
tcagtgcctt tgttgttgtg tttgtattca gttctattgc aataatttgt ttagctgttc    1440 tttataggggt gcttaagtgc ctgaagattg ccccaaggaa agttctgaat ccactaatgt    1500
ggatcacagc cttcatcaga tggatatata agaagatggt tgccagagtg gcagacaaca    1560
ttaatcaagt gaacagggaa ataggatgga tggaaggagg tcagttggtt ctagggaacc   1620 ctgccccctat tcctcgtcat gccccaatcc cacgttatag cacatacctg atgttattat    1680
```

```
tgattgtctc atatgcatca gcatgttcag aactgattca ggcaagctcc agaatcacca    1740
cttgctctac agagggtgtt aacaccaagt gtagactgtc tggcacagca ttgatcagag    1800
cagggtcagt tggggcagag gcttgtttga tgttgaaggg ggtcaaggaa gatcaaacca    1860
agttcttaaa gataaaaact gtctcaagtg agctatcatg cagggagggc cagagttatt    1920
ggactgggtc ctttagccct aaatgtttga gctcaaggag atgccacctt gtcgggaat    1980
gccatgtgaa taggtgtctg tcttggaggg acaatgaaac ttcagcagag ttttcatttg    2040
ttggggaaag cacgaccatg cgagagaata agtgttttga gcaatgtgga ggatgggggt    2100
gtgggtgttt caatgtgaac ccatcttgct tatttgtgca cacgtatctg cagtcagtta    2160
gaaaagaggc ccttagagtt tttaactgta tcgactgggt gcataaactc actctagaga    2220
tcacagactt tgatggctct gtttcaacaa tagacttggg agcatcatct agccgtttca    2280
caaactgggg ttcagttagc ctctcactgg acgcagaggg catctcaggc tcaaatagct    2340
tttctttcat tgagagccca ggtaaagggt atgcaattgt tgatgagcca ttctcagaaa    2400
ttcctcggca agggttcttg ggggagatca ggtgcaattc agagtcctca gtcctgagtg    2460
ctcatgaatc atgccttagg gcaccaaacc ttatctcata caagcccatg atagatcaat    2520
tggagtgcac aacaaatctg attgatccct ttgttgtctt tgagagggt tctctgccac    2580
agacaaggaa tgataaaacc tttgcagctt caaaaggaaa tagaggtgtt caagctttct    2640
ctaagggctc tgtacaagct gatctaactc tgatgtttga caattttgag gtggactttg    2700
tgggagcagc cgtatcttgt gatgccgcct tcttaaattt gacaggttgc tattcttgca    2760
atgcagggc cagggtctgc ctgtctatca catccacagg aactggatct ctctctgccc    2820
acaataagga tgggtctctg catatagtcc ttccatcaga gaatggaaca aaagaccagt    2880
gtcagatact acacttcact gtgcctgaag tagaggagga gtttatgtac tcttgtgatg    2940
gagatgagcg gcctctgttg gtgaaggga ccctgatagc cattgatcca tttgatgata    3000
ggcgggaagc agggggggaa tcaacagttg tgaatccaaa atctggatct tggaatttct    3060
ttgactggtt ttctggactc atgagttggt ttggagggcc tcttaaaact atactcctca    3120
tttgcctgta tgttgcatta tcaattgggc tcttttttcct ccttatatat cttggaagaa    3180
caggcctctc taaaatgtgg cttgctgcca ctaagaaggc ctcatagatc agtacgtgta    3240
aaagcaatat gttgaaataa gtagacacaa gcaaacctaa ttatgtaagt gttgtacaga    3300
taggtcaaat tattggaata tccaagctta gaaacttatg caataatact ttagatgtaa    3360
gcttagttgt aatttggggt ggtggggtga ggcagcagca gtctcaagtg cttgtgaata    3420
ttctagttgg cgtaatcgtc ttttgccaga ttagctggga attaaactaa ctcttttgaag   3480
ttgcaccggc ctttgtgtgg gtcggcatgg catctccacc tcctcgcggt ccgacctggg    3540
catccgaagg aggacgtcgt ccactcggat ggctaaggga gcaagcttag cggtcaccgc    3600
tgagcaataa ctagcataac cccttggggc tctaaacgg gtcttgaggg gttttttaag    3660
ccgaattcgt aatcatgtca tagctgtttc ctgtgtgaaa ttgttatccg ctcacaattc    3720
cacacaacat acgagccgga agcataaagt gtaaagcctg gggtgcctaa tgagtgagct    3780
aactcacatt aattgcgttg cgctcactgc ccgctttcca gtcgggaaac ctgtcgtgcc    3840
agctgcatta atgaatcggc caacgcgcgg ggagaggcgg tttgcgtatt gggcgctctt    3900
ccgcttcctc gctcactgac tcgctgcgct cggtcgttcg gctgcggcga gcggtatcag    3960
ctcactcaaa ggcggtaata cggttatcca cagaatcagg gataacgca ggaaagaaca    4020
tgtgagcaaa aggccagcaa aaggccagga accgtaaaaa ggccgcgttg ctggcgtttt    4080
```

```
tccataggct ccgcccccct gacgagcatc acaaaaatcg acgctcaagt cagaggtggc   4140
gaaacccgac aggactataa agataccagg cgtttccccc tggaagctcc ctcgtgcgct   4200
ctcctgttcc gaccctgccg cttaccggat acctgtccgc ctttctccct tcgggaagcg   4260
tggcgctttc tcatagctca cgctgtaggt atctcagttc ggtgtaggtc gttcgctcca   4320
agctgggctg tgtgcacgaa ccccccgttc agcccgaccg ctgcgcctta tccggtaact   4380
atcgtcttga gtccaacccg gtaagacacg acttatcgcc actggcagca gccactggta   4440
acaggattag cagagcgagg tatgtaggcg gtgctacaga gttcttgaag tggtggccta   4500
actacggcta cactagaaga acagtatttg gtatctgcgc tctgctgaag ccagttacct   4560
tcggaaaaag agttggtagc tcttgatccg gcaaacaaac caccgctggt agcggtggtt   4620
tttttgtttg caagcagcag attacgcgca gaaaaaaagg atctcaagaa gatcctttga   4680
tcttttctac ggggtctgac gctcagtgga acgaaaactc acgttaaggg attttggtca   4740
tgagattatc aaaaaggatc ttcacctaga tccttttaaa ttaaaaatga agttttaaat   4800
caatctaaag tatatatgag taaacttggt ctgacagtta ccaatgctta atcagtgagg   4860
cacctatctc agcgatctgt ctatttcgtt catccatagt tgcctgactc cccgtcgtgt   4920
agataactac gatacgggag ggcttaccat ctggccccag tgctgcaatg ataccgcgag   4980
acccacgctc accggctcca gatttatcag caataaacca gccagccgga agggccgagc   5040
gcagaagtgg tcctgcaact ttatccgcct ccatccagtc tattaattgt tgccgggaag   5100
ctagagtaag tagttcgcca gttaatagtt tgcgcaacgt tgttgccatt gctacaggca   5160
tcgtggtgtc acgctcgtcg tttggtatgg cttcattcag ctccggttcc caacgatcaa   5220
ggcgagttac atgatccccc atgttgtgca aaaaagcggt tagctccttc ggtcctccga   5280
tcgttgtcag aagtaagttg gccgcagtgt tatcactcat ggttatggca gcactgcata   5340
attctcttac tgtcatgcca tccgtaagat gcttttctgt gactggtgag tactcaacca   5400
agtcattctg agaatagtgt atgcggcgac cgagttgctc ttgcccggcg tcaatacggg   5460
ataataccgc gccacatagc agaactttaa aagtgctcat cattggaaaa cgttcttcgg   5520
ggcgaaaact ctcaaggatc ttaccgctgt tgagatccag ttcgatgtaa cccactcgtg   5580
cacccaactg atcttcagca tcttttactt tcaccagcgt ttctgggtga gcaaaaacag   5640
gaaggcaaaa tgccgcaaaa aagggaataa gggcgacacg gaaatgttga atactcatac   5700
tcttcctttt tcaatattat tgaagcattt atcagggtta ttgtctcatg agcggataca   5760
tatttgaatg tatttagaaa aataaacaaa taggggttcc gcgcacattt ccccgaaaag   5820
tgccacctga cgtctaagaa accattatta tcatgacatt aacctataaa aataggcgta   5880
tcacgaggcc ctttcgtctc gcgcgtttcg gtgatgacgg tgaaaacctc tgacacatgc   5940
agctcccgga gacggtcaca gcttgtctgt aagcggatgc cgggagcaga caagcccgtc   6000
agggcgcgtc agcgggtgtt ggcgggtgtc ggggctggct taactatgcg gcatcagagc   6060
agattgtact gagagtgcac cattcgacgc tctcccttat gcgactcctg cattaggaag   6120
cagcccagta gtaggttgag gccgttgagc accgccgccg caaggaatgg tgcatgcaag   6180
gagatggcgc ccaacagtcc cccggccacg gggcctgcca ccatacccac gccgaaacaa   6240
gcgctcatga gcccgaagtg gcgagcccga tcttccccat cggtgatgtc ggcgatatag   6300
gcgccagcaa ccgcacctgt ggcgccggtg atgccggcca cgatgcgtcc ggcgtagagg   6360
atctggctag cgatgaccct gctgattggt tcgctgacca tttccgggtg cgggacggcg   6420
```

```
ttaccagaaa ctcagaaggt tcgtccaacc aaaccgactc tgacggcagt ttacgagaga    6480
gatgataggg tctgcttcag taagccagat gctacacaat taggcttgta catattgtcg    6540
ttagaacgcg gctacaatta atacataacc ttatgtatca tacacatacg atttaggtga    6600
cactatagaa tacaagcttg ggctgcaggt cgactaatac gactcactat ag            6652
```

RECOMBINANT RIFT VALLEY FEVER (RVF) VIRUSES AND METHODS

CROSS-REFERENCE TO RELATED APPLICATIONS

This is a divisional of U.S. application Ser. No. 12/809,561, filed Jun. 18, 2010, issued as U.S. Pat. No. 8,673,629 on Mar. 18, 2014. which is the U.S. National Stage of International Application No. PCT/US2008/087023, filed Dec. 16, 2008, published in English under PCT Article 21(2), which claims the benefit of U.S. Provisional Application No. 61/016,065, filed Dec. 21, 2007, and U.S. Provisional Application No. 61/042,987, filed Apr. 7, 2008. All of the above-listed applications are herein incorporated by reference in their entirety.

FIELD

This disclosure concerns recombinant RVF viruses comprising deletions in viral virulence genes. These recombinant viruses can be used as vaccines to prevent RVF virus infection. This disclosure further relates to a reverse genetics system used to generate recombinant RVF viruses.

BACKGROUND

Rift Valley fever (RVF) virus (family Bunyaviridae, genus *Phlebovirus*) is a mosquito-borne pathogen of both livestock and humans found throughout Africa and more recently the Arabian Peninsula. Historically, RVF virus has been the cause of either low-level endemic activity or large explosive epizootics/epidemics of severe disease throughout its range (Findlay et al., *Lancet* ii:1350-1351, 1931; Jouan et al., *Res. Virol.* 140:175-186, 1989; Ringot et al., *Emerg. Infect. Dis.* 10:945-947, 2004; Woods et al., *Emerg. Infect. Dis.* 8:138-144, 2002). RVF outbreaks are characterized by economically disastrous "abortion storms" with newborn animal mortality approaching 100% among livestock, especially sheep and cattle (Coetzer et al., *J. Vet. Res.* 49:11-17, 1982; Easterday et al., *Am. J. Vet. Res.* 23:470-479, 1962; Rippy et al., *Vet. Pathol.* 29:495-502, 1992).

Human infections typically occur either from an infected mosquito bite, percutaneous/aerosol exposure during the slaughter of infected animals, or via contact with aborted fetal materials. Human RVF disease is primarily a self-limiting febrile illness that in a small percentage (about 1-2%) of cases can progress to more serious and potentially lethal complications including hepatitis, delayed onset encephalitis, retinitis, blindness, or a hemorrhagic syndrome with a hospitalized case fatality of 10-20% (Madani et al., *Clin. Infect. Dis.* 37:1084-1092, 2003; McIntosh et al., *S. Afr. Med. J.* 58:03-806, 1980). Excessively heavy rainfall in semi-arid regions often precedes large periodic outbreaks of RVF virus activity, allowing for the abundant emergence of transovarially infected *Aedes* spp. mosquitoes and subsequent initiation of an outbreak by transmission of virus to livestock and humans via infected mosquito feeding (Linthicum et al., *Science* 285:397-400, 1999; Swanepoel et al., *Contributions to Epidemiology and Biostatistics* 3:83-91, 1981). The association with abnormally heavy rains provides some ability to predict periods and regions of high disease risk, which in turn provides a potential window of opportunity for targeted vaccination programs if a safe, inexpensive and highly efficacious single dose vaccine were available.

The ability of RVF virus to cross international and geographic boundaries and strain veterinary and public health infrastructures is well documented. In 1977, RVF virus was reported for the first time north of the Sahara desert where an extremely large outbreak affecting more than 200,000 people occurred along the Nile River basin in Egypt (Meegan et al., *Contributions to Epidemiology and Biostatistics* 3:100-113, 1981). Approximately ten years later in 1987, a large outbreak occurred in western Africa along the border of Mauritania and Senegal affecting an estimated 89,000 individuals (Jouan et al., *Res. Virol.* 140:175-186, 1989). Later, the virus was isolated for the first time outside of Africa (across the Red sea) in Saudi Arabia and Yemen and was found to be the cause of a large epizootic/epidemic in 2000 with an estimated 2000 human cases and 245 deaths (Anonymous, *Morb. Mortal. Wkly. Rep.* 49:982-5, 2000; Centers for Disease Control and Prevention, *Morb. Mortal. Wkly. Rep.* 49:1065-1066, 2000; Shoemaker et al., *Emerg. Infect. Dis.* 8:1415-1420, 2002).

Most recently, in late 2006 to early 2007, following heavy rainfall in eastern Africa, RVF virus emerged as the cause of a widespread outbreak that eventually resulted in 1062 reported human cases and 315 reported deaths. Associated with the outbreak were substantial economic losses among livestock in southern Somalia, Kenya, and northern Tanzania (Anonymous, *Morb. Mortal. Wkly. Rep.* 56:73-76, 2007). The ability of RVF virus to cause explosive outbreaks in previously unaffected regions accompanied by high morbidity and mortality during RVF epizootics/epidemics highlights the importance of developing high throughput screening tools for potential antiviral therapeutic agents and the development of safe and efficacious vaccines for this significant veterinary and public health threat.

SUMMARY

Disclosed are RVF viruses that are highly attenuated, immunogenic and contain precise molecular markers allowing for the differentiation of naturally infected and vaccinated animals (DIVA). Provided herein are recombinant RVF viruses, wherein the genome of the recombinant RVF viruses comprise (i) a full-length L segment; (ii) a full-length M segment or an M segment comprising a complete deletion of the NSm open reading frame (ORF); and (iii) an S segment comprising a complete deletion of the NSs ORF. In one embodiment, the NSs ORF of the recombinant RVF virus is replaced by the ORF of a reporter gene.

Also provided are immunogenic compositions comprising one or more of the recombinant RVF viruses described herein and a pharmaceutically acceptable carrier. Further provided is a method of immunizing a subject against RVF virus infection, comprising administering to the subject an immunogenic composition disclosed herein. The immunogenic compositions can be used for vaccination of livestock or humans.

Further provided is a collection of plasmids comprising (i) a plasmid encoding a full-length anti-genomic copy of the L segment of RVF virus; (ii) a plasmid encoding a full-length anti-genomic copy of the M segment of RVF virus, or an anti-genomic copy of the M segment of RVF virus comprising a complete deletion of the NSm ORF; and (iii) a plasmid encoding an anti-genomic copy of the S segment of RVF virus, wherein the S segment comprises a complete deletion of the NSs ORF. In some embodiments, the plasmids further comprise a T7 promoter and a hepatitis delta virus ribozyme. In one example, the NSs ORF of the S segment plasmid is replaced by the ORF of a reporter gene, such as a green fluorescent protein. Also provided are isolated host cells comprising a collection of plasmids provided herein.

Further provided is a method of preparing a recombinant RVF virus for immunization of a subject, comprising (i) transfecting cultured cells with the collection of plasmids described herein; (ii) incubating the cells for 1 to 5 days; and (iii) collecting recombinant RVF virus from the cell supernatant.

Also provided are recombinant RVF viruses, wherein the genome of the recombinant RVF viruses comprise a full-length L segment, a full-length M segment and a full-length S segment, wherein the S segment further encodes the ORF of a reporter gene.

A reverse genetics system for producing recombinant RVF virus is also provided. The reverse genetics system consists of three plasmids, a plasmid that encodes an antigenomic copy of an S segment, a plasmid that encodes an M segment and a plasmid that encodes an L segment of RVF virus, wherein each plasmid comprises a T7 promoter and a hepatitis delta virus ribozyme. Further provided are recombinant RVF viruses produced using the reverse genetics system described herein.

The foregoing and other features and advantages will become more apparent from the following detailed description of several embodiments, which proceeds with reference to the accompanying figures.

BRIEF DESCRIPTION OF THE FIGURES

FIG. 1A is a schematic depiction of the rRVF cDNA plasmid constructions used to generate the rRVF virus stocks. FIG. 1B is a series of images showing direct live cell UV imaging of Vero E6 cells 24 hours after infection with each recombinant rRVF virus (expressing eGFP). FIG. 1C is a series of images showing Vero E6 cells 24 hours after infection with rRVF-NSs-(Ala)$_3$GFP or rRVF-NSs(Ala)$_{10}$GFP viruses at an MOI of 1. Cells were fixed and stained with monoclonal antibodies specific for eGFP, RVF NSs and counterstained with DAPI to confirm intranuclear co-localization of eGFP and NSs.

FIGS. 3A-3D are a series of images showing representative results of indirect fluorescent testing of serum collected from (FIG. 3A) WF rats surviving challenge with RVF virus; (FIG. 3B) vaccinated WF rats (day 26 post-vaccination); (FIG. 3C) negative control sham inoculated rats (day 26 post-vaccination); and (FIG. 3D) naturally infected convalescent livestock (goat) sera obtained during the RVF virus outbreak in Saudi Arabia in 2000. The presence of anti-NP antibodies (left panels) and anti-NSs antibodies (right panels) is detected using Vero E6 cells expressing either NP or NSs, respectively. To confirm intranuclear accumulation of anti-NSs antibody, cells were counterstained with DAPI.

FIGS. 4A and 4B are tables showing data obtained from a vaccination pilot study (FIG. 4A) and challenge study (FIG. 4B).

SEQUENCE LISTING

Figure 2:
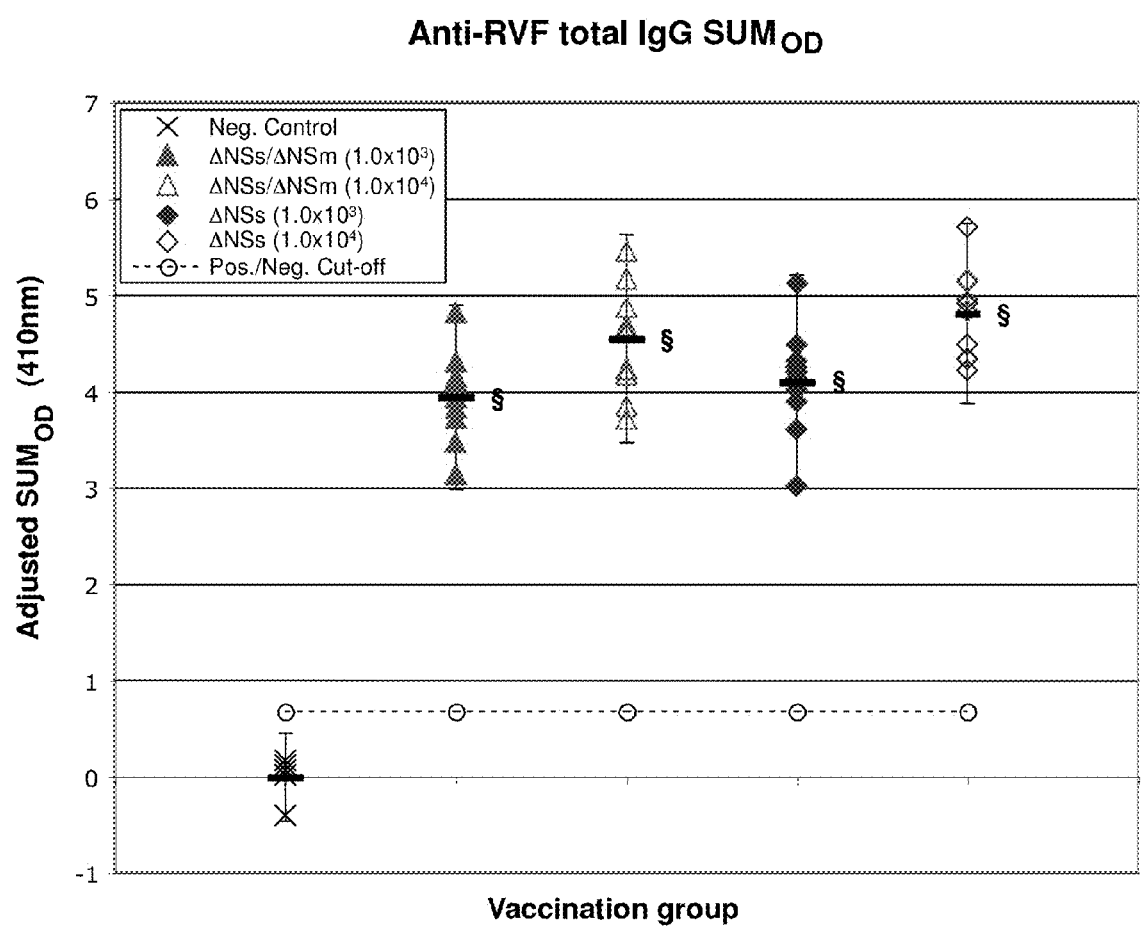
FIG. 2 is a graph showing the results of anti-RVF virus total IgG adjusted SUM$_{OD}$ ELISA testing of all vaccinated (40) and sham inoculated (5) control animals at day 26 post-immunization. A positive/negative cut-off value was established as the mean+3 standard deviations of the sham inoculated SUM$_{OD}$ values (open circles-dashed line). §=Significant differences between vaccinated and control groups (p-value <0.05).
Figure 5:
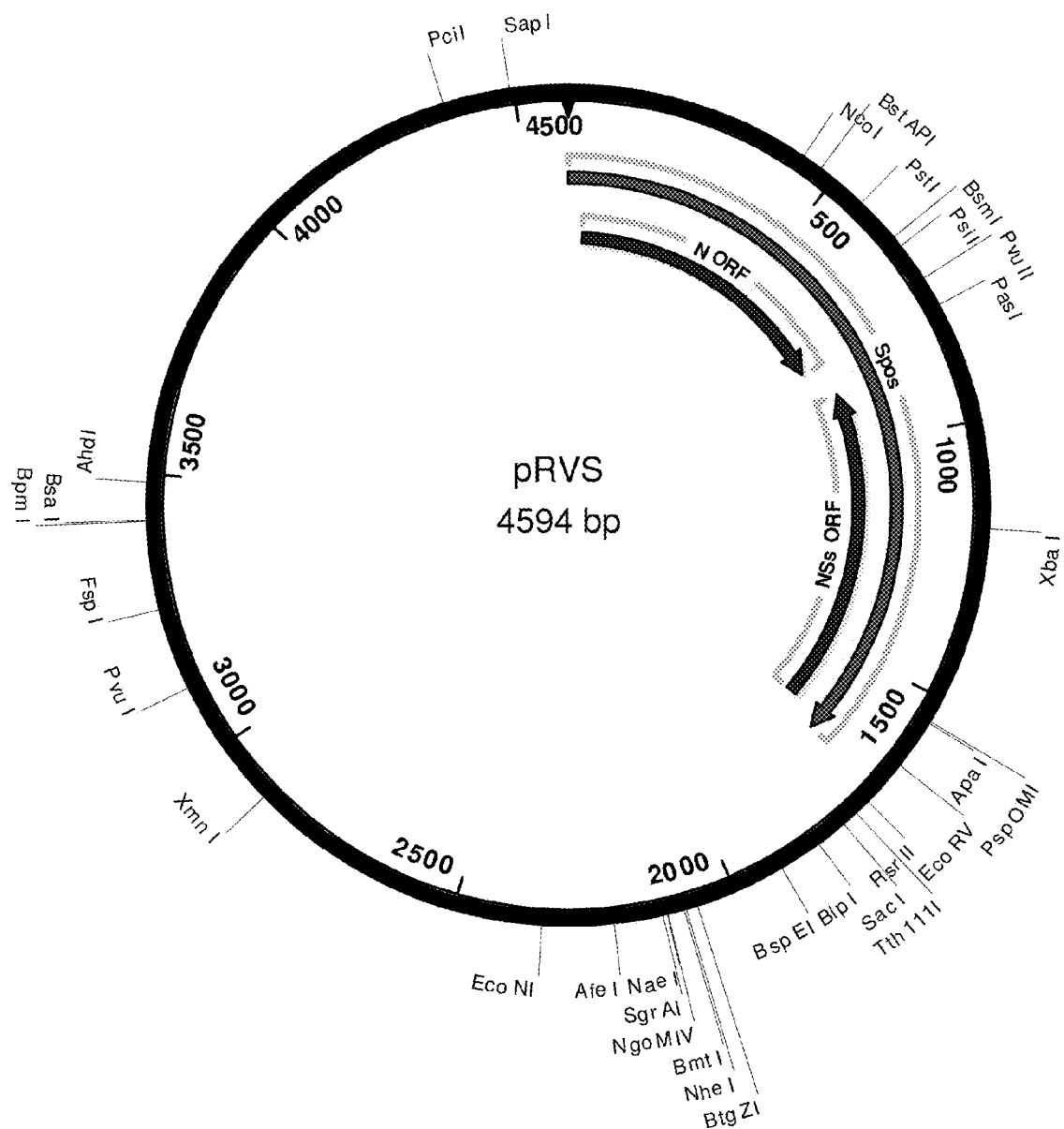
FIG. 5 is a plasmid map of pRVS.
Figure 6:
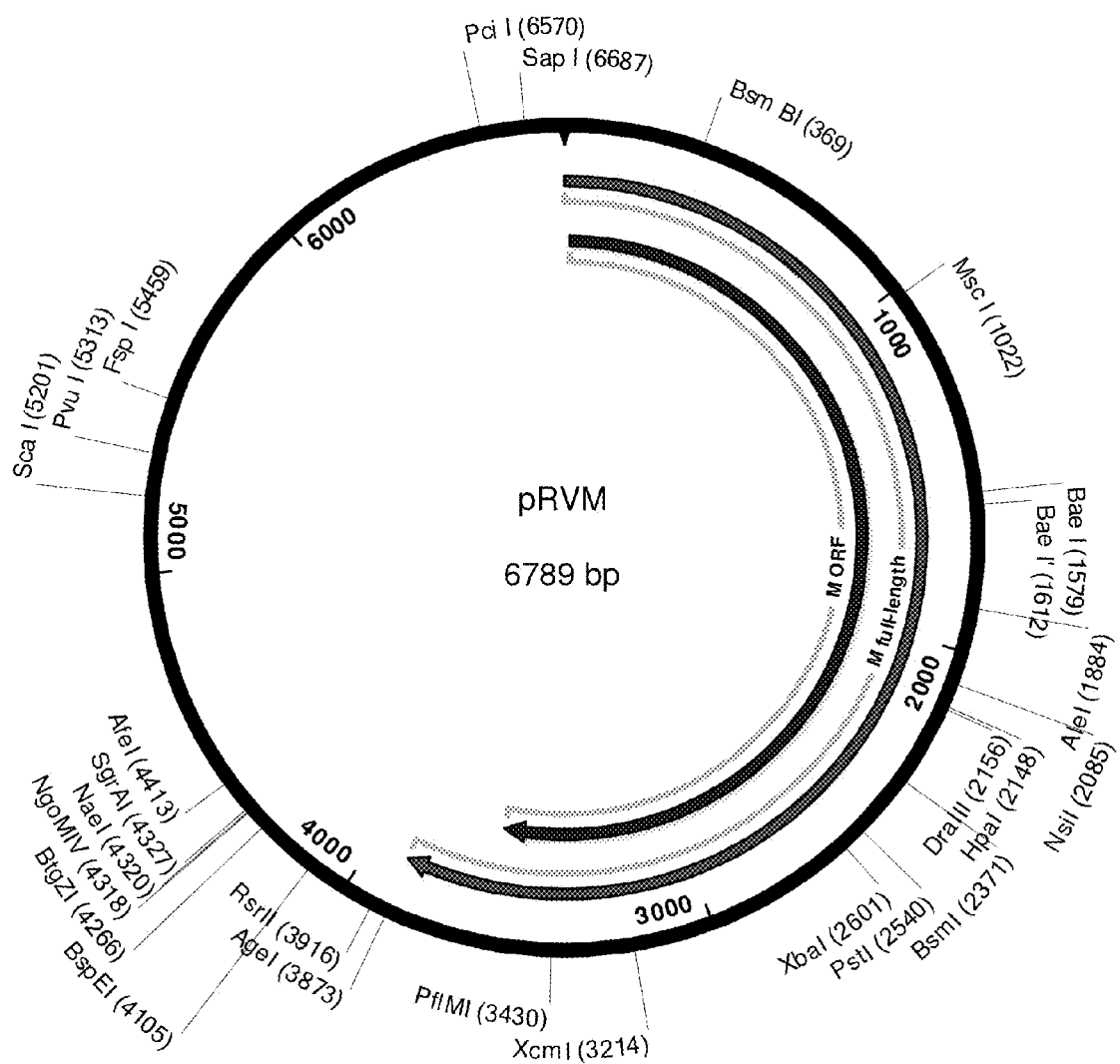
FIG. 6 is a plasmid map of pRVM.
Figure 7:
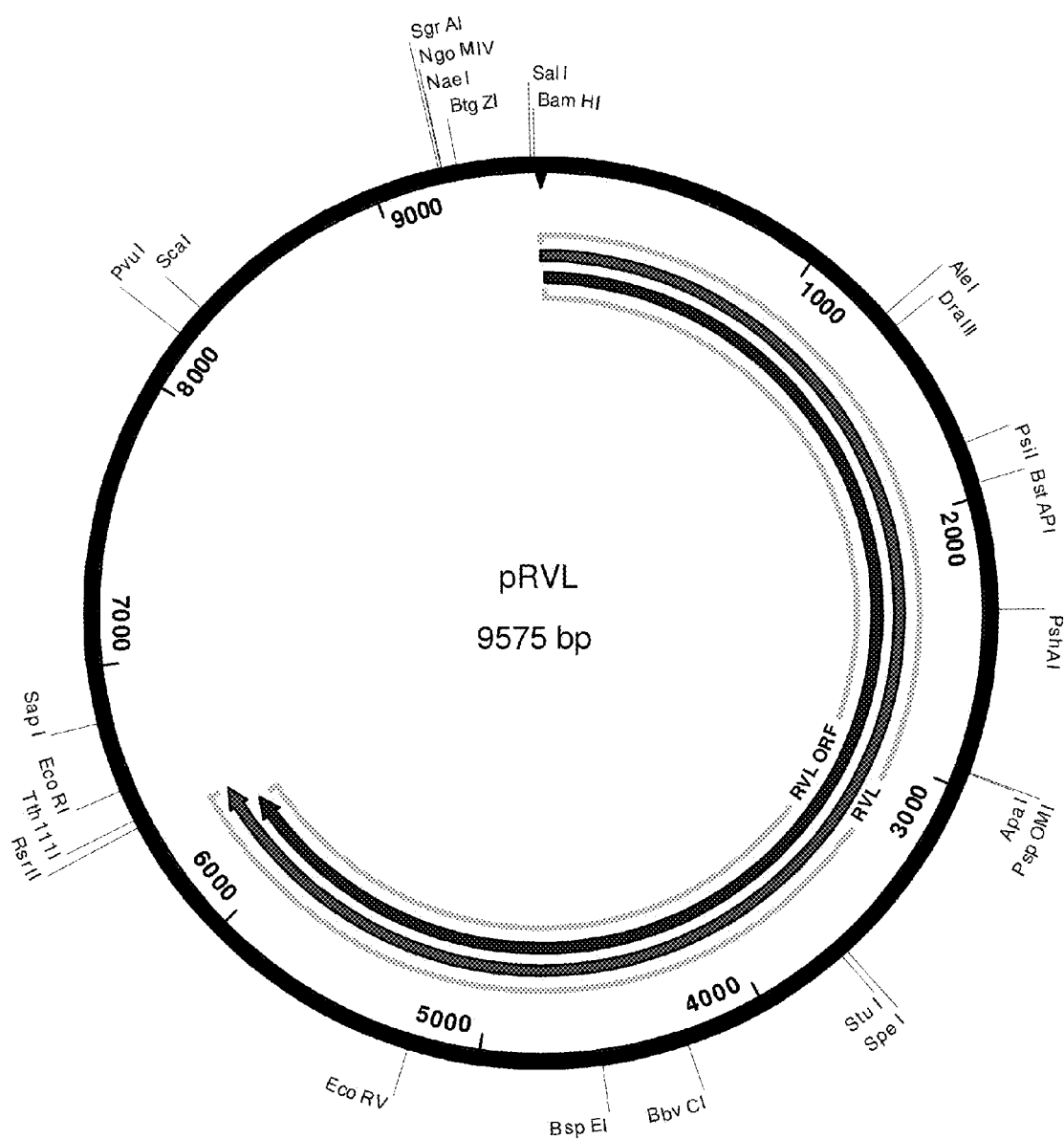
FIG. 7 is a plasmid map of pRVL.
Figure 8:
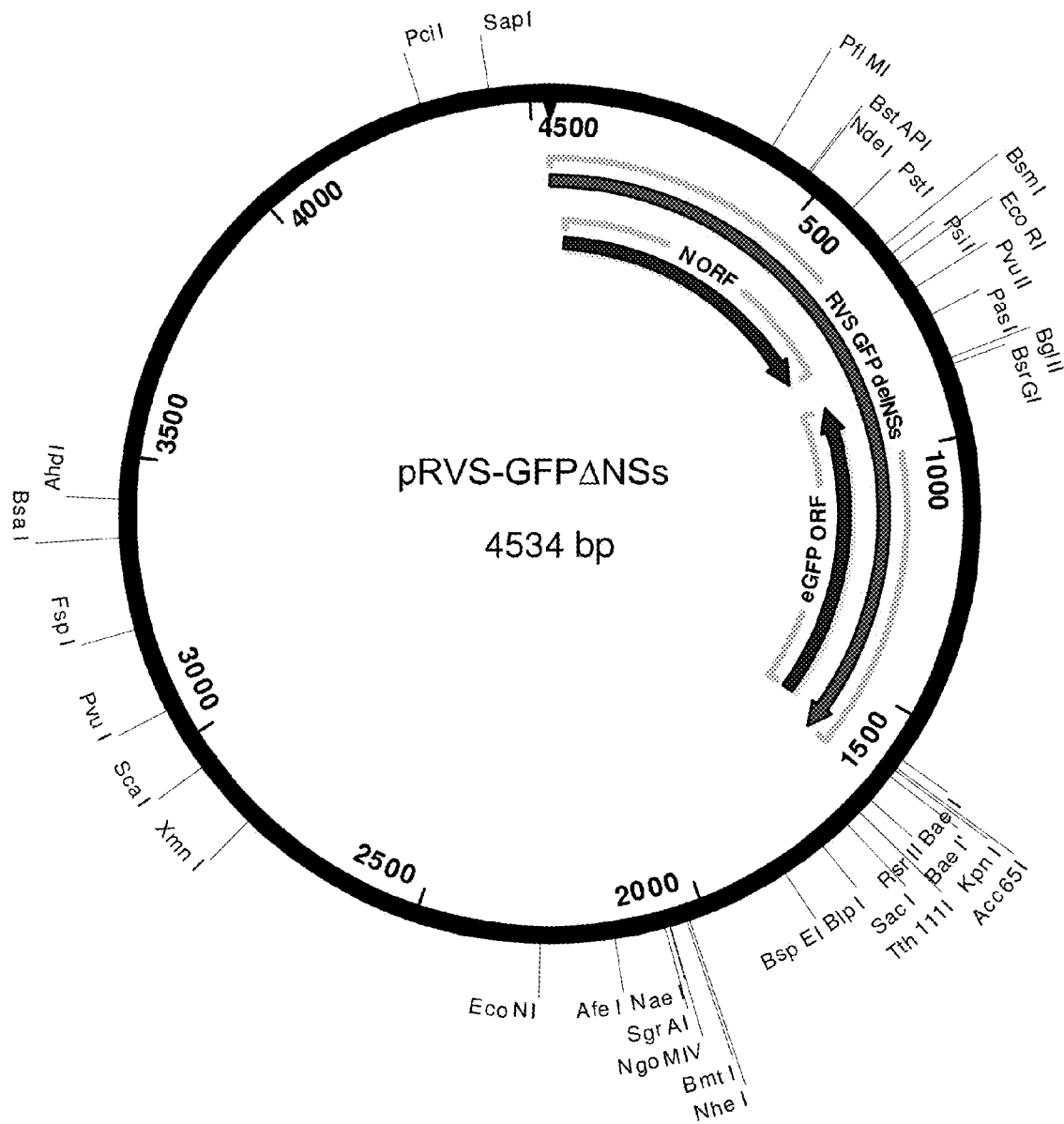
FIG. 8 is a plasmid map of pRVS-GFPΔNSs.
Figure 9:
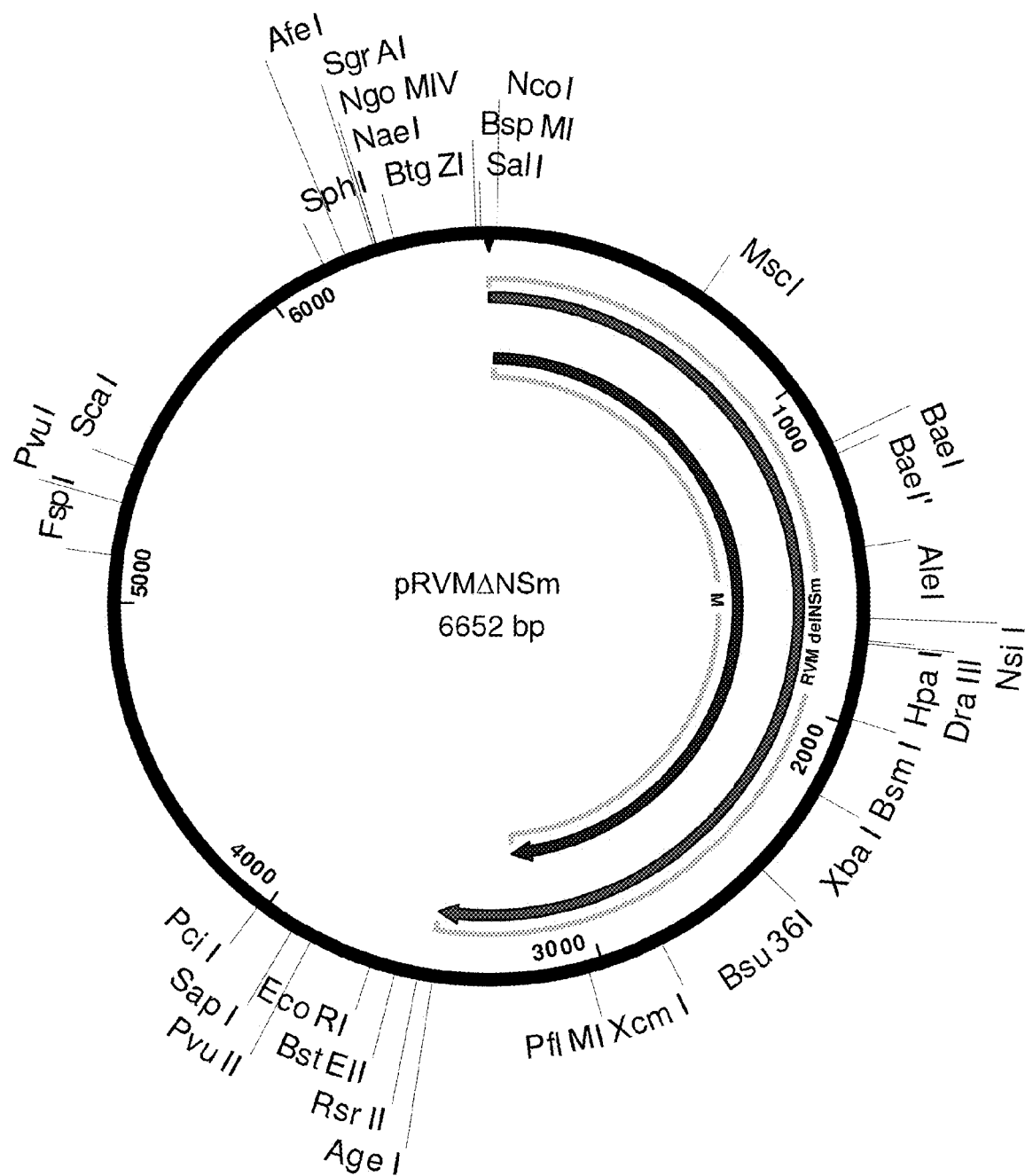
FIG. 9 is a plasmid map of pRVMΔNSm.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text filed, created on Jan. 24, 2014, 58.9 KB. In the accompanying sequence listing:

SEQ ID NO: 1 is the nucleotide sequence of the S segment of wild-type RVF virus strain ZH501, deposited under GenBank Accession No. DQ380149 on Jan. 31, 2007.

SEQ ID NO: 2 is the nucleotide sequence of the M segment of wild-type RVF virus strain ZH501, deposited under GenBank Accession No. DQ380200 on Jan. 31, 2007.

SEQ ID NO: 3 is the nucleotide sequence of the L segment of wild-type RVF virus strain ZH501, deposited under GenBank Accession No. DQ375406 on Jan. 31, 2007.

SEQ ID NO: 4 is the nucleotide sequence of primer RVS-35/KpnI.

SEQ ID NO: 5 is the nucleotide sequence of primer RVS+827/BglII.

SEQ ID NO: 6 is the nucleotide sequence of primer eGFP+1/KpnI.

SEQ ID NO: 7 is the nucleotide sequence of primer eGFP-720/BglII.

SEQ ID NO: 8 is the nucleotide sequence of primer RVS-829rev/KpnI.

SEQ ID NO: 9 is the nucleotide sequence of primer NSsGFP+10Ala/Fwd.

SEQ ID NO: 10 is the nucleotide sequence of primer NSsGFP+10Ala/Rev.

SEQ ID NO: 11 is the nucleotide sequence of plasmid pRVS.

SEQ ID NO: 12 is the nucleotide sequence of plasmid pRVM.

SEQ ID NO: 13 is the nucleotide sequence of plasmid pRVL.

SEQ ID NO: 14 is the nucleotide sequence of plasmid pRVS-GFPΔNSs.

SEQ ID NO: 15 is the nucleotide sequence of the plasmid pRVMΔNSm.

DETAILED DESCRIPTION

I. Abbreviations

BSL Bio-safety level
CPE Cytopathic effect
DIVA Differentiation of naturally infected and vaccinated animals
eGFP Enhanced green fluorescent protein
HRP Horseradish peroxidase
IFA Immunofluorescence assay
LD Lethal dose
MOI Multiplicity of infection
NP Nucleoprotein
NS Non-structural
OIE Office International des Epizooties
ORF Open reading frame
PFU Plaque-forming unit
PRNT Plaque reduction neutralization titers RNA Ribonucleic acid
RT-PCR Reverse transcriptase polymerase chain reaction
RVF Rift Valley fever
SQ Subcutaneously
USDA United States Department of Agriculture
WF Wistar-furth
WOAH World Organization for Animal Health II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Ambisense: Refers to a genome or genomic segments having both positive sense and negative sense portions. For example, the S segment of a Phlebovirus, such as Rift Valley fever virus, is ambisense, encoding nucleoprotein (NP) in the negative sense and the non-structural protein (NSs) in the positive sense.

Animal: Living multi-cellular vertebrate organisms, a category that includes, for example, mammals and bird. Mammals include, but are not limited to, humans, non-human primates, dogs, cats, horses, sheep and cows. The term mammal includes both human and non-human mammals.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a RVF virus antigen.

Anti-genomic: As used herein, "anti-genomic" refers to a genomic segment of a virus that encodes a protein in the orientation opposite to the viral genome. For example, Rift valley fever virus is a negative-sense RNA virus. However, the S segment is ambisense, encoding proteins in both the positive-sense and negative-sense orientations. "Anti-genomic" refers to the positive-sense orientation, while "genomic" refers to the negative-sense orientation.

Attenuated: In the context of a live virus, the virus is attenuated if its ability to infect a cell or subject and/or its ability to produce disease is reduced (for example, eliminated) compared to a wild-type virus. Typically, an attenuated virus retains at least some capacity to elicit an immune response following administration to an immunocompetent subject. In some cases, an attenuated virus is capable of eliciting a protective immune response without causing any signs or symptoms of infection. In some embodiments, the ability of an attenuated virus to cause disease in a subject is reduced at least about 10%, at least about 25%, at least about 50%, at least about 75% or at least about 90% relative to wild-type virus.

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain to internal stop codons.

Hepatitis delta virus ribozyme: A non-coding, catalytic RNA from the hepatitis delta virus. Ribozymes catalyze the hydrolysis of their own phosphodiester bonds or those of other RNA molecules.

Host cell: In the context of the present disclosure, a "host cell" is a cell of use with the RVF virus reverse genetics systems described herein. A suitable host cell is one that is capable of transfection with and expression of the plasmids of the RVF virus reverse genetics system. In one embodiment, the host cell is a cell expressing the T7 polymerase, such as, but not limited to BSR-T7/5 cells (Buchholz et al., *J. Virol.* 73(1):251-259, 1999).

Immune response: A response of a cell of the immune system, such as a B-cell, T-cell, macrophage or polymorphonucleocyte, to a stimulus such as an antigen. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection).

Immunogen: A compound, composition, or substance which is capable, under appropriate conditions, of stimulating an immune response, such as the production of antibodies or a T-cell response in an animal, including compositions that are injected or absorbed into an animal. As used herein, as "immunogenic composition" is a composition comprising an immunogen.

Immunize: To render a subject protected from an infectious disease, such as by vaccination.

Isolated: An "isolated" biological component (such as a nucleic acid, protein or virus) has been substantially separated or purified away from other biological components (such as cell debris, or other proteins or nucleic acids). Biological components that have been "isolated" include those components purified by standard purification methods. The term also embraces recombinant nucleic acids, proteins or viruses, as well as chemically synthesized nucleic acids or peptides.

Linker: One or more amino acids that serve as a spacer between two polypeptides of a fusion protein.

Livestock: Domesticated animals reared in an agricultural setting as a source of food or to provide labor. The term "livestock" includes, but is not limited to, cattle, deer, donkeys, goats, horses, mules, rabbits and sheep.

ORF (open reading frame): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more recombinant RVF viruses, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Plasmid: A circular nucleic acid molecule capable of autonomous replication in a host cell.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In one embodiment, the promoter is a T7 promoter (from bacteriophage T7).

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. In one embodiment, recombinant RVF virus is generated using the reverse genetics system described herein. In some examples, the recombinant RVF viruses comprise one or more deletions in a viral virulence factor, such as NSs and/or NSm. In other examples, the recombinant RVF viruses comprise a heterologous gene, such as a reporter gene.

Reporter gene: A reporter gene is a gene operably linked to another gene or nucleic acid sequence of interest (such as a promoter sequence). Reporter genes are used to determine whether the gene or nucleic acid of interest is expressed in a cell or has been activated in a cell. Reporter genes typically have easily identifiable characteristics, such as fluorescence, or easily assayed products, such as an enzyme. Reporter genes can also confer antibiotic resistance to a host cell or tissue. Reporter genes include, for example, GFP (or eGFP) or other fluorescence genes, luciferase, β-galactosidase and alkaline phosphatase.

Reverse genetics: Refers to the process of introducing mutations (such as deletions, insertions or point mutations) into the genome of an organism or virus in order to determine the phenotypic effect of the mutation. For example, introduction of a mutation in a specific viral gene enables one to determine the function of the gene.

Rift Valley fever (RVF) virus: A virus belonging to the family Bunyaviridae and genus *Phlebovirus*. RVF virus has a single-stranded, negative-sense genome composed of three genome segments, S, M and L. The S segment is an ambisense genome segment, meaning it encodes proteins in both the positive-sense and negative-sense orientations. The RVF virus genome encodes both structural and non-structural proteins. A "structural" protein is a protein found in the virus particle, whereas a "non-structural" protein is only expressed in a virus-infected cell. RVF virus structural proteins include nucleoprotein (NP or N, used interchangeably), two glycoproteins (Gn and Gc) and the viral RNA-dependent RNA polymerase (L protein). Non-structural RVF virus proteins include NSs, NSm and the NSm+Gn fusion protein. As used herein, a "full-length" RVF virus genome segment is one containing no deletions. Full-length genome segments can contain mutations or substitutions, but retain the same length as the wild-type virus. A "complete deletion" of an ORF of a RVF virus genome segment means either every nucleotide encoding the ORF is deleted from genome segment, or nearly every nucleotide encoding the ORF is deleted such that no proteins are translated from the ORF. Thus, a "complete deletion" includes genome segments retaining up to ten nucleotides encoding the ORF, such as one, two, three, four, five, six, seven, eight, nine or ten nucleotides. A number of RVF virus strains have been identified. In one embodiment described herein, the RVF virus strain is ZH501.

As used herein, plasmids encoding full-length RVF virus S, M and L genome segments are referred to as pRVS, pRVM, and pRVL, respectively. The S segment plasmid containing the eGFP ORF in place of the complete NSs ORF is referred to as pRVS-GFPΔNSs. The M segment plasmid containing a complete deletion of the NSm ORF is referred to as pRVM-ΔNSm. The recombinant RVF viruses based upon the ZH501 genome that are generated using reverse genetics are referred to as either rRVF or rZH501. For example, recombinant RVF virus generated using the pRVS-GFPΔNSs plasmid (and wild-type M and L plasmids), is referred to as rRVF-ΔNSs:GFP or rZH501-ΔNSs:GFP. Similarly, recombinant RVF virus generated using the pRVS-GFPΔNSs plasmid and pRVM-ΔNSm plasmid (and wild-type L plasmid), referred to as rRVF-ΔNSs:GFP-ΔNSm or rZH501-ΔNSs:GFP-ΔNSm. Recombinant RVF virus comprising wild-type M and L segments, and an S segment encoding an NSs-eGFP fusion protein with a three alanine residue linker, is referred to as rRVF-NSs(Ala)$_3$GFP or rZH501—NSs(Ala)$_3$GFP). If the fusion protein comprises a ten alanine residue linker, the recombinant virus is referred to as rRVF-NSs(Ala)$_{10}$GFP or rZH501—NSs(Ala)$_{10}$GFP.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Subject: Living multi-cellular vertebrate organisms, a category that includes both human and non-human mammals. Subjects include veterinary subjects, including livestock such as cows and sheep, and non-human primates.

Therapeutically effective amount: A quantity of a specified agent sufficient to achieve a desired effect in a subject being treated with that agent. For example, this may be the amount of a recombinant RVF virus useful for eliciting an immune response in a subject and/or for preventing infection by RVF virus. Ideally, in the context of the present disclosure, a therapeutically effective amount of a recombinant RVF virus is an amount sufficient to increase resistance to, prevent, ameliorate, and/or treat infection caused by RVF virus in a subject without causing a substantial cytotoxic effect in the subject. The effective amount of a recombinant RVF virus useful for increasing resistance to, preventing, ameliorating, and/or treating infection in a subject will be dependent on, for example, the subject being treated, the manner of administration of the therapeutic composition and other factors.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A preparation of immunogenic material capable of stimulating an immune response, administered for the prevention, amelioration, or treatment of infectious or other types of disease. The immunogenic material may include attenuated or killed microorganisms (such as attenuated viruses), or antigenic proteins, peptides or DNA derived from them. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein are RVF virus vaccine candidates that are highly attenuated, immunogenic and contain precise molecular markers allowing for the differentiation of naturally infected and vaccinated animals (DIVA). The recombinant RVF viruses described herein, which in some embodiments contain complete deletions of one or both of the major virus virulence factors, NSs and NSm, are highly attenuated in vivo, induce robust anti-RVF antibody responses, provide protection from virulent virus challenge and allow for the assessment of vaccination status in animals on the basis of NSs/NP serology. Further provided are recombinant RVF viruses comprising a reporter moiety, such as eGFP, which have a variety of applications, including as live virus research tools that can be useful for the rapid screening of antiviral therapeutic compounds.

Provided herein are recombinant RVF viruses, wherein the genome of the recombinant RVF viruses comprise (i) a full-length L segment; (ii) a full-length M segment or an M segment comprising a complete deletion of the NSm open reading frame (ORF); and (iii) an S segment comprising a complete deletion of the NSs ORF. In one embodiment, the NSs ORF of the recombinant RVF virus is replaced by the ORF of a reporter gene. Reporter genes include, but are not limited to genes encoding fluorescent proteins, enzymes or antibiotic resistance. Any gene that produces a protein with a functional readout can be used as the reporter gene. In one example, the reporter gene is a green fluorescent protein (GFP), such as enhanced GFP (eGFP).

The genome of the recombinant RVF viruses provided herein can be derived from any strain or variant of RVF virus. In some embodiments, the genome is derived from ZH501, ZH548, SA75 or SPB 9800523. In a preferred embodiment, the genome is derived from RVF virus strain ZH501. The sequences of the S, M and L segments of the ZH501 strain are deposited under GenBank Accession Nos. DQ380149 (SEQ ID NO: 1), DQ380200 (SEQ ID NO: 2) and DQ375406 (SEQ ID NO: 3), respectively. The nucleotide sequences of the S, M and L segments need not be 100% identical to the sequences provided herein. In some examples, the S, M and L segments are at least 80%, at least 85%, at least 90%, at least 95%, or at least 99% identical to a known or disclosed RVF virus S, M or L segment, such as the S, M and L segments set forth as SEQ ID NO: 1, SEQ ID NO: 2 and SEQ ID NO: 3, respectively.

Also provided are immunogenic compositions comprising the recombinant RVF viruses described herein and a pharmaceutically acceptable carrier. Suitable pharmaceutical carriers are described herein and are well known in the art. The pharmaceutical carrier used depends on a variety of factors, including the route of administration. In one embodiment, the immunogenic composition further comprises an adjuvant. The adjuvant can be any substance that improves the immune response to the recombinant RVF virus.

Further provided is a method of immunizing a subject against RVF virus infection, comprising administering to the subject an immunogenic composition disclosed herein. In one embodiment, the subject is livestock. Livestock includes, but is not limited to sheep and cattle. In another embodiment, the subject is a human. In one example, the immunogenic composition is administered in a single dose. In another embodiment, the immunogenic composition is administered in multiple doses, such as two, three or four doses. When administered in multiple doses, the time period between doses can vary. In some cases, the time period is days, weeks or months. The immunogenic composition can be administered using any suitable route of administration. Generally, the recombinant RVF viruses are administered parenterally, such as intramuscularly, intravenously or subcutaneously.

Further provided is a collection of plasmids comprising (i) a plasmid encoding a full-length anti-genomic copy of the L segment of RVF virus; (ii) a plasmid encoding a full-length anti-genomic copy of the M segment of RVF virus, or an anti-genomic copy of the M segment of RVF virus comprising a complete deletion of the NSm ORF; and (iii) a plasmid encoding an anti-genomic copy of the S segment of RVF virus, wherein the S segment comprises a complete deletion of the NSs ORF. In some embodiments, the plasmids further comprise a T7 promoter and a hepatitis delta virus ribozyme. In one example, the NSs ORF of the S segment plasmid is replaced by the ORF of a reporter gene. In one example, the reporter gene is green fluorescent protein. In some embodiments, the RVF virus is ZH501.

In one embodiment, the nucleotide sequence of the S segment plasmid is at least 95% identical to the nucleotide sequence of SEQ ID NO: 14. In particular examples, the nucleotide sequence of the S segment plasmid comprises the nucleotide sequence of SEQ ID NO: 14. In another embodiment, the nucleotide sequence of the M segment plasmid is at least 95% identical to the nucleotide sequence of SEQ ID NO: 12. In particular examples, the nucleotide sequence of the M segment plasmid comprises the nucleotide sequence of SEQ ID NO: 12. In another embodiment, the nucleotide sequence of the M segment plasmid is at least 95% identical to the nucleotide sequence of SEQ ID NO: 15. In particular examples, the nucleotide sequence of the M segment plasmid comprises the nucleotide sequence of SEQ ID NO: 15. In another embodiment, the nucleotide sequence of the L segment plasmid is at least 95% identical to the nucleotide sequence of SEQ ID NO: 13. In particular examples, the nucleotide sequence of the L segment plasmid comprises the nucleotide sequence of SEQ ID NO: 13.

Also provided are isolated host cells comprising the collection of plasmids provided herein. In one embodiment, the cells express T7 polymerase.

Further provided is a method of preparing a recombinant RVF virus for immunization of a subject, comprising (i) transfecting cultured cells with the collection of plasmids described herein; (ii) incubating the cells for 1 to 5 days; and (iii) collecting recombinant RVF virus from the cell supernatant. In one embodiment, the cells express T7 polymerase.

Further provided are recombinant RVF viruses, wherein the genome of the recombinant RVF viruses comprise a full-length L segment, a full-length M segment and a full-length S segment, wherein the S segment further encodes the ORF of a reporter gene. In one embodiment, the S segment encodes a NSs-reporter gene fusion protein. In one aspect, the reporter gene is fused to the C-terminus of NSs. In some examples, the fusion protein further comprises a linker. The linker can be any suitable combination of one or more amino acids. In one embodiment, the linker comprises 3 to 10 alanine residues. In another embodiment, the reporter gene is GFP.

Also provided herein is a reverse genetics system for producing recombinant RVF virus. The reverse genetics system consists of three plasmids, wherein a first plasmid encodes an anti-genomic copy of a S segment, a second plasmid encodes an anti-genomic copy of a M segment and a third plasmid encodes an anti-genomic copy of a L segment of RVF virus, and wherein each plasmid comprises a T7 promoter and a hepatitis delta virus ribozyme. In some embodiments, the RVF virus is ZH501. In some embodiments, the S, M and L segments are wild-type S, M and L segments. In another embodiment, the S segment comprises a deletion of the NSs ORF. In another embodiment, the M segment comprises a deletion of the NSm ORF. In another embodiment, the S segment comprises a deletion of the NSs ORF and the M segment comprises a deletion of the NSm ORF.

In one embodiment, the nucleotide sequence of the S segment plasmid is at least 95% identical to the nucleotide sequence of SEQ ID NO: 11. In particular examples, the nucleotide sequence of the S segment plasmid comprises the nucleotide sequence of SEQ ID NO: 11. In another embodiment, the nucleotide sequence of the S segment plasmid is at least 95% identical to the nucleotide sequence of SEQ ID NO: 14. In particular examples, the nucleotide sequence of the S segment plasmid comprises the nucleotide sequence of SEQ ID NO: 14. In another embodiment, the nucleotide sequence of the M segment plasmid is at least 95% identical to the nucleotide sequence of SEQ ID NO: 12. In particular examples, the nucleotide sequence of the M segment plasmid comprises the nucleotide sequence of SEQ ID NO: 12. In another embodiment, the nucleotide sequence of the M segment plasmid is at least 95% identical to the nucleotide sequence of SEQ ID NO: 15. In particular examples, the nucleotide sequence of the M segment plasmid comprises the nucleotide sequence of SEQ ID NO: 15. In another embodiment, the nucleotide sequence of the L segment plasmid is at least 95% identical to the nucleotide sequence of SEQ ID NO: 13. In particular examples, the nucleotide sequence of the L segment plasmid comprises the nucleotide sequence of SEQ ID NO: 13.

Typically, the three plasmids are transfected simultaneously into cells expressing T7 polymerase. After a sufficient period of time to allow for production of recombinant virus, such as about 1 to about 5 days, recombinant RVF virus is collected from the cell supernatant.

Further provided are recombinant RVF viruses produced using the reverse genetics system described herein. In some examples, the recombinant RVF viruses comprise a deletion in one or more viral virulence factors. In one embodiment, the recombinant viruses comprise a complete deletion of the NSs ORF. In another embodiment, the recombinant viruses comprise a complete deletion of the NSm ORF. In yet another embodiment, the recombinant viruses comprise a deletion in both the NSs and NSm ORFs. The recombinant RVF viruses can be used for both research and therapeutic purposes. For example, the recombinant RVF viruses described herein are suitable for use as vaccines to prevent, treat or ameliorate RVF virus infection in livestock and humans.

IV. Rift Valley Fever Virus Genome and Encoded Proteins

Like other members of the genus *Phlebovirus*, RVF virus has a negative-sense, single-stranded tripartite RNA genome composed of the S, M and L segments (Schmaljohn, and Hooper, Bunyaviridae: The Viruses and their Replication In Fields' Virology, Lippincott Williams & Wilkins, Philadelphia, Pa., 2001). The small (S) segment (about 1.6 kB) encodes, in an ambisense fashion, the virus nucleoprotein (NP) in the genomic (−) orientation, and the non-structural (NSs) protein in the anti-genomic (+) orientation (Albarino et al., *J. Virol.* 81:5246-5256, 2007). The medium (M) segment (about 3.8 kB) encodes a least four nested proteins in a single ORF, including two structural glycoproteins, Gn and Gc, and two nonstructural proteins, the 14 kD NSm and a 78 kD NSm+Gn fusion (Gerrard et al, *Virology* 359:459-465, 2007; Gerrard and Nichol, *Virology* 357:124-133, 2007). The M segment contains five conserved in-frame AUG-methionine start codons within the NSm protein coding region at anti-genomic sense positions 21, 135, 174, 411 and 426. Alternate utilization of the AUGs at positions 21 or 135 results in expression of the 14 kDa NSm protein and the 78 kD NSm+Gn fusion protein (Suzich et al., *J. Virol.* 64:1549-1555, 1990, Gerrard and Nichol, *Virology* 357:124-133, 2007). The large (L) segment (about 6.4 kB) encodes the viral RNA-dependent RNA polymerase (L protein).

RVF virus NP and L proteins are required for viral RNA synthesis (Ikegami et al., *J. Virol.* 79:5606-5615, 2005; Lopez et al., *J. Virol.* 69:3972-3979, 1995). Gn and Gc are believed to mediate binding to an as yet unidentified receptor. The 78 kD NSm+Gn fusion protein has been reported to be dispensable for viral replication in cell culture (Won et al., *J. Virol.* 80:8274-8278, 2006).

Both nonstructural genes (NSs and NSm) have been reported to function as virus virulence factors and determinants of mammalian host pathogenesis (Bird et al., *Virology* 362:10-15, 2007; Vialat et al., *J. Virol.* 74:1538-1543, 2000; Won et al., *J. Virol.* 24:13335-13345, 2007). NSs mediates the pan-downregulation of mRNA production by inhibition of RNA polymerase II activity (Billecocq et al., *J. Virol.* 78:9798-9806, 2004; Le May et al., *Cell* 116:541-550, 2004). Via this mechanism, the NSs protein performs a critical role in mammalian host pathogenesis by indirectly disrupting the host cell antiviral response (Bouloy et al., *J. Virol.*, 75:1371-1377, 2001; Muller et al., *Am. J. Trop. Med. Hyg.* 53:405-411, 1995; Vialat et al., *J. Virol.* 74:1538-1543, 2000).

Studies of the non-structural gene located on the RVF virus M segment (NSm) indicate it is dispensable for efficient RVF virus growth in both IFN-competent and IFN-deficient cell culture (Gerrard et al, *Virology* 359:459-465, 2007; Won et al., *J. Virol.* 80:8274-8278, 2006). However, further work utilizing a highly sensitive animal model revealed that recombinant RVF virus lacking the entire NSm coding region (rRVF-ΔNSm) was attenuated yet retained the ability to cause either acute-onset lethal hepatic necrosis or delayed-onset lethal neurologic disease in a minority (44%) of animals (Bird et al., *Virology* 362:10-15, 2007). Other studies have shown that NSm functions as a virus virulence factor by suppressing the host cell apoptotic pathway following infection (Won et al., *J. Virol.* 24:13335-13345, 2007).

V. Reverse Genetics System for RVF Virus

The ability to generate recombinant viruses containing selected mutations and/or deletions is a powerful tool for the development of virus vaccines. Reverse genetics systems have been described for a few viruses of the Bunyaviridae family, including Bunyamvera virus (Bridgen and Elliott, *Proc. Natl. Acad. Sci. USA* 93:15400-15404, 1996) and La Crosse virus (Blakqori and Weber, *J. Virol.* 79:10420-10428, 2005). Recently, a reverse genetics system for a vaccine strain (MP-12) of RVF virus was reported (U.S. Pre-Grant Publication No. 2007/0122431, herein incorporated by reference).

The recombinant RVF viruses described herein are generated using an optimized reverse genetics system capable of rapidly generating wild-type and mutant viruses (Bird et al., *Virology* 362:10-15, 2007; Gerrard et al., *Virology* 359:459-465, 2007, each of which is herein incorporated by reference). The RVF virus reverse genetics system is a T7 RNA polymerase-driven plasmid-based genetic system based on the genome of the virulent RVF virus Egyptian isolate ZH501. This system, described in detail in Bird et al. (*Virology* 362:10-15, 2007) and in the Examples below, includes three plasmids expressing anti-genomic copies of the S, M and L segments of ZH501. As used herein, the plasmids are referred to as the pRVS, pRVM and pRVL plasmids, respectively.

Rescue of recombinant viruses is accomplished by simultaneous transfection of the three anti-genomic sense plasmids into cells stably expressing T7 polymerase (for example, BSR-T7/5 cells). The genome segments of each plasmid are flanked by a T7 promoter, which enables generation of the primary RNA transcript, and the hepatitis delta virus ribozyme, which removes extraneous nucleotides from the 3' end of the primary transcriptional products. The T7 RNA polymerase generated transcripts are identical copies of the RVF virus genome segments, with the exception of an extra G nucleotide on the 5' end derived from the T7 promoter. When expressed in transfected host cells, the pRVS, pRVM and pRVL plasmids generate anti-genomic sense copies of the S, M and L segments, respectively.

In one embodiment, the recombinant RVF viruses are generated using an S-segment plasmid that comprises a deletion in the NSs gene. In one example, the deletion is a deletion of the entire NSs ORF. In one aspect, the NSs ORF is replaced by the eGFP ORF. In another embodiment, the recombinant RVF viruses are generated using an S-segment plasmid comprising a deletion in the NSs gene and an M-segment plasmid comprising a deletion in the NSm ORF. In one example, the deletion is a deletion of the entire NSm ORF. In another embodiment, the recombinant RVF viruses are generated using full-length S, M and L plasmids, wherein one of the plasmids further encodes eGFP. In one example, the eGFP ORF is encoded by the S plasmid as a NSs-eGFP fusion protein.

VI. Use of Recombinant RVF Viruses

Recombinant RVF viruses generated using the reverse genetics system described herein can be used for both research and therapeutic purposes. Using this system, recombinant RVF viruses can be generated that contain precisely defined deletions of major virus virulence factors on one or more genome segments. For example, viruses can be produce that contain deletions of NSs and/or NSm. Accordingly, such recombinant RVF viruses can be used as vaccines to prevent infection of livestock and humans with wild-type RVF virus. The recombinant RVF viruses described herein can also be used as live-virus research tools, particularly those viruses that incorporate reporter genes, for instance a fluorescent protein such as GFP. For example, these viruses can be used for high-throughput screening of antiviral compounds in vitro.

Efforts to prevent RVF virus infection via vaccination began shortly after the first isolation of the virus in 1931 (Findlay and Daubney, *Lancet* ii:1350-1351, 1931). These earliest vaccines (MacKenzie, *J. Pathol. Bacteriol.* 40:65-73, 1935) and several that followed, including the currently available TSI-GSD-200 preparation, relied on formalin inactivation of live wild-type virus (Pittman et al., *Vaccine* 18:181-189, 1999; Randall et al., *J. Immunol.* 89:660-671, 1962). While capable of eliciting protective immune responses among livestock and humans, these inactivated vaccines typically require a series of 2 or 3 initial inoculations, followed by regular booster vaccinations to achieve and maintain protection (Pittman et al., *Vaccine* 18:181-189, 1999; Swanepoel et al., "Rift Valley fever" in Infectious Diseases of livestock with special reference to South Africa, pages 688-717, Oxford university Press, Cape Town). However, multiple dosing and annual vaccination regimens are logistically difficult to implement and expensive to maintain, and thus are of limited practical value in resource-poor settings, especially in regard to control of RVF virus infection in livestock in enzootic settings. In addition, there have been problems in the past with quality control and "inactivated" vaccines causing disease.

In an effort to eliminate the necessity of booster inoculations, several live-attenuated vaccine candidates were developed for RVF virus with some, such as the Smithburn neurotropic strain, being employed in Africa. These vaccine candidates have relied upon the random introduction of attenuating mutations via serial passage in suckling mouse brain or tissue culture, in vitro passage in the presence of chemical mutagens, such as 5-fluorouracil, or as naturally occurring virus isolates (such as the Smithburn neurotropic strain, the Kenyan-IB8 strains, MP-12, or the Clone 13 isolate) (Caplen et al., *J. Gen. Virol.* 66:2271-2277, 1985; Coackley, *J. Pathol. Bacteriol.* 89:123-131, 1965; Moussa et al., *Am. J. Trop. Med. Hyg.* 35:660-662, 1986; Muller et al.,

*Am J. Trop. Med. Hyg.* 53:405-411, 1995; Rossi and Turell, *J. Gen. Virol.* 69:817-823, 1988; Smithburn, *Br. J. Exp. Pathol.* 30:1-16, 1949).

Due to the technical limitations of these procedures, and the lack of complete genome sequence for many of the historically derived RVF virus vaccines, the exact underlying molecular mechanisms of attenuation for many of these live-attenuated RVF virus vaccines is either unknown (Smithburn neurotropic strain or Kenyan-IB8) or reliant on the combinatorial effects of multiple nucleotide or amino acid substitutions (MP-12) (Saluzzo and Smith, *Vaccine* 8:369-375, 1990; Takehara et al., *Virology* 169:452-457, 1989). Experimental and field experience with existing live-attenuated RVF virus vaccines demonstrated that in certain instances these vaccines retain the ability to cause teratogenic effects, abortion, and neural pathology in livestock or animal models. Thus, widespread use of these live-attenuated vaccines is problematic, especially in non-endemic areas, or during inter-epizootic/epidemic periods (Hunter et al., *Onderstepoort J. Vet. Res.* 69:95-98, 2002; Morrill et al., *Am. J. Vet. Res.* 58:1104-1109, 1997; Morrill et al., *Am. J. Vet. Res.* 58:1110-1114, 1997; Morrill and Peters, *Vaccine* 21:2994-3002, 2003).

While useful in many situations, several distinct disadvantages exist among live attenuated RNA virus vaccines prepared by the traditional techniques discussed above. Live-attenuated vaccines reliant on single or multiple nucleotide substitutions are at increased risk for reversion to virulent phenotypes due to the inherently high rate of viral RNA polymerase errors. The loss of attenuation via this mechanism among livestock and human live vaccines has been documented (Berkhout et al., *J. Virol.* 73:1138-1145, 1999; Catelli et al., *Vaccine* 24:6476-6482, 2006; Halstead et al., *Am. J. Trop. Med. Hyg.* 33:672-678, 1984; Hopkins and Yoder, *Avian Dis.* 30:221-223, 1986; Rahimi et al., *J. Clin. Virol.* 39:304-307, 2007).

The potential for a similar reversion event among live RVF virus vaccines dependent on attenuating nucleotide mutation was illustrated by recent genomic analyses of RVF virus that revealed an overall molecular evolution rate (~$2.5 \times 10^4$ nucleotide substitutions/site/year) similar to other single-stranded RNA viruses (Bird et al., *J. Virol.* 81:2805-2816, 2007). Due to error-prone polymerases, live-attenuated RNA virus vaccines prepared by multiple serial passage techniques involved in virus attenuation inherently consist of a complex mixture of genomic micro-variants. In contrast, the origin of reverse genetics derived virus vaccine candidates is advantageous in that vaccine stocks can be generated directly or following limited amplification steps from precisely defined DNA plasmids. This approach allows for the simple production of virus vaccines following good manufacturing processes (GMP) with higher levels of genetic homogeneity.

Another significant drawback of all previously generated live-attenuated RVF virus vaccines is that they do not allow for differentiation of naturally infected from vaccinated animals (DIVA). This ability is important to augment efforts to contain an accidental or intentional release of wild-type RVF virus in previously unaffected areas (Henderson, *Biologicals* 33:203-209, 2005). As a high consequence pathogen, RVF virus has been classified as a category A Select Agent as defined by the United States Department of Health and Human Services and the United States Department of Agriculture (USDA), and is listed as a high consequence agent with potential for international spread (List A) by the Office International des Epizooties (OIE) (Le May et al., *Cell* 116:541-550, 2004) of the World Organization for Animal Health (WOAH), thus greatly increasing the consequences for international livestock trade following the introduction of RVF virus into previously unaffected countries or epizootics in enzootic areas (USDA, 7 CFR Part 331 and 9 CFR Part 121, Federal Register RIN 0579-AB47:13241-13292, 2005). Currently, OIE regulations require surveillance and absence of RVF virus activity for 2 years following an outbreak before resumption of disease free status and the subsequent easing of import/export trade restrictions (International Office of Epizootics, Terrestrial Animal Health Code, XI:2.2.14.1, 2007). The use of any current commercially available livestock vaccines does not permit the differentiation of vaccinated from naturally infected livestock, thus contraindicating the use of prophylactic vaccination in countries wishing to retain disease free status, or in those with ongoing/endemic RVF virus activity.

Thus, disclosed herein are infectious recombinant RVF viruses, generated using reverse genetics, containing either complete deletions of major virus virulence factors, NSs (rZH501-ΔNSs:GFP) or NSs and NSm (rZH501-ΔNSs:GFP-ΔNSm), which confer attenuated phenotypes in vivo, and which allow for the serologic differentiation of naturally infected and vaccinated animals by presence/absence of anti-RVF NP/anti-RVF NSs antibodies. As described herein, in vivo testing of these recombinant RVF (rRVF) viruses demonstrated that they were highly immunogenic and efficacious in the prevention of severe RVF virus disease and lethality (FIG. 2 and FIG. 4). In an initial pilot study, animals developed high end-point titers (≥1:400) of total anti-RVF virus IgG by day 21 post-vaccination that were significantly higher than sham inoculated controls (p-value <0.05, Table 1). At no observed time point post-vaccination did any animal develop disease symptoms or vaccine virus induced viremia (FIG. 4).

Additional testing in a larger follow-up study confirmed these results with the majority of animals generating robust total anti-RVF IgG responses with typical titers ≥1:6400 by day 26 post-vaccination. As with the pilot study, no vaccine virus induced viremia was detected. The immunologic response generated in the ΔNSs/ΔNSm virus vaccinated animals was significantly higher than controls (p-value <0.05) and was sufficient to confer complete protection from both clinical illness and lethality in 100% of vaccinated animals given a known lethal challenge dose of wild-type RVF virus (FIG. 4).

Direct comparisons of the level of protective immunity ($PRNT_{50}$ or total IgG) titers with previous studies utilizing other RVF virus vaccines are difficult due to vaccine used and species level differences in immunity. However, earlier studies utilizing the 3 dose regimen (day 0, 7 and 28) of inactivated TSI-GSD-200 vaccine in the WF rat model demonstrated protective efficacy against virulent virus challenge at $PRNT_{80}$ titers >1:40 (Anderson et al., *Vaccine* 9:710-714, 1991). Later, a large retrospective analysis of human volunteers (n=598), receiving the same recommended 3-dose regimen of this inactivated vaccine were found to develop mean $PRNT_{80}$ titers of 1:237 (Pittman et al., *Vaccine* 18:181-189, 1999). Additionally, a large study of the pathogenesis and neurovirulence of the live-attenuated MP-12 vaccine in rhesus macaques demonstrated $PRNT_{80}$ titers among vaccinated animals of ≥1:640 (Morrill and Peters, *Vaccine* 21:2994-3002, 2003). As described herein, inoculation with a single dose of the recombinant RVF viruses resulted in mean $PRNT_{50}$ titers ranging from 1:640 to 1:7040, indicating that the level of neutralizing antibody is similar to or greater than that demonstrated in earlier RVF vaccine studies using multiple doses in animal model systems or among human volunteers.

Thus, the enhanced safety, attenuation, and reduced possibility of reversion to full virulence (via either RVF virus polymerase nucleotide substitution or gene segment reassortment with field-strains) afforded by the double genetic deletions of the entire RVF virus NSs and NSm genes, does not diminish overall vaccine efficacy. A high level of protective immunity was induced by a single dose of the rRVF viruses disclosed herein, with 37 of 40 total vaccinated animals developing a potentially sterilizing immunity as determined by the lack of any detectable post-challenge viremia (FIG. 4).

As described herein, animals immunized with either recombinant RVF virus do not have detectable anti-NSs antibodies. Thus, given the high-level anti-NSs antibody in survivor control animals, DIVA will be possible among animals immunized with these candidate vaccines based on the presence/absence of anti-NSs antibody (FIGS. 3A-C). Anti-NSs antibodies have also been detected in the serum of naturally infected convalescent livestock obtained during the outbreak in Saudi Arabia in 2000 (FIG. 3D), and in humans. Therefore, the use of these recombinant RVF viruses, combined with the further development of rapid ELISA or solid matrix-based differential detection assays for anti-NP/anti-NSs antibodies, can provide a robust DIVA field screening tool.

In addition, the recombinant RVF viruses described herein routinely grew to high titers in tissue culture and provided protective immunity following a single injection, thus likely reducing the overall economic cost of production, and potentially eliminating the need for resource intensive follow-up booster inoculations. Additionally, the precisely defined attenuating deletions and use of cDNA technology eliminates the potential risk of reversion to, or contamination from, virulent wild-type virus inherent in serial passaged or inactivated vaccine preparations, and may ease the federal/national regulatory approval process. While the recombinant RVF viruses can be targeted towards veterinary medical use, and thus indirectly the prevention of human RVF disease, the candidate vaccines can also provide effective prophylactic protection for humans, such as those in high risk occupational settings, or in recognized risk groups following natural or intentional introduction of RVF virus into previously unaffected areas.

VII. Administration of Recombinant RVF Virus for Vaccination

Recombinant RVF viruses, or immunogenic compositions thereof, can be administered to a subject by any of the routes normally used for introducing recombinant virus into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Immunogenic compositions are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose administered to a subject in the context of the present disclosure should be sufficient to induce a beneficial therapeutic response in a subject over time, or to inhibit or prevent RVF virus infection. The dose required will vary from subject to subject depending on the species, age, weight and general condition of the subject, the severity of the infection being treated, the particular immunogenic composition being used and its mode of administration. An appropriate dose can be determined by one of ordinary skill in the art using only routine experimentation.

Provided herein are pharmaceutical compositions (also referred to as immunogenic compositions) which include a therapeutically effective amount of the recombinant RVF viruses alone or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

The recombinant RVF viruses described herein can be administered alone or in combination with other therapeutic agents to enhance antigenicity. For example, the recombinant viruses can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2): 122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

The following examples are provided to illustrate certain particular features and/or embodiments. These examples should not be construed to limit the disclosure to the particular features or embodiments described.

EXAMPLES

Example 1

Optimized Reverse Genetics System for Generation of Recombinant RVF Virus

This example describes the development of an improved reverse genetics system for generation of recombinant RVF viruses. The recombinant RVF viruses described herein are generated using an optimized reverse genetics system capable of rapidly generating wild-type and mutant viruses (Bird et al., *Virology* 362:10-15, 2007, herein incorporated by reference). The RVF virus reverse genetics system is a T7 RNA polymerase-driven plasmid-based genetic system that requires only three plasmids. Each plasmid individually expresses an anti-genomic copy of either the S, M or L segment. In this specific example, the S, M and L segments are derived from the genome of the virulent Egyptian RVF virus isolate ZH501. Nucleotide sequences of ZH501 S, M and L segments are provided herein as SEQ ID NOs: 1-3, respectively.

Rescue of recombinant viruses is accomplished by simultaneous transfection of the three anti-genomic sense plasmids into cells stably expressing T7 polymerase (for example, BSR-T7/5 cells). The genome segments of each plasmid are flanked by a T7 promoter, which enables generation of the primary RNA transcript, and the hepatitis delta virus ribozyme, which removes extraneous nucleotides from the 3' end of the primary transcriptional products. The T7 RNA polymerase generated transcripts are identical copies of the RVF-encoding plasmids, with the exception of an extra G nucleotide on the 5' end derived from the T7 promoter.

A previously reported method of producing recombinant RVF virus required the use of five expression plasmids (Gerrard et al., *Virology* 359:459-465, 2007). In addition to expression plasmids encoding RVF virus S, M and L segments, this system included plasmids encoding RVF virus N protein and RNA-dependent RNA polymerase (L protein). Northern blot and 3'RACE revealed that the S plasmid used in that system produced low levels of full length S-segment anti-genomic replication products. To produce a more efficient S segment plasmid, the full length S RNA from ZH501 was re-cloned into a version of the plasmid vector that was modified to remove the multiple cloning site. Within this backbone context, levels of N protein expression were significantly increased, allowing for subsequent rescue of recombinant virus without the need for a support plasmid encoding the N protein.

In addition, the optimized system described herein includes an M segment clone in which two non-synonymous mutations were corrected to match the wild-type sequence, allowing for exact in vivo comparisons between recombinant and wild-type viruses. These corrections were made in both the full-length M segment and the ΔNSm plasmid by site directed mutagenesis and restriction fragment exchange. These changes included removal of the XhoI restriction site. After incorporating these changes into the reverse genetics system, virus rescue was accomplished by simultaneous transfection of only the three anti-genomic sense plasmids (either wild-type S, M and L segments, or deletion mutants thereof). The nucleotide sequences of exemplary wild-type S, M and L plasmids, and plasmids comprising deletions in the S and M segments, are provided herein as SEQ ID NOs: 11-15. Maps of each of these plasmids are shown in FIGS. 5-9.

After complete lysis of transfected cells, cell supernatants containing rescued viruses were clarified, diluted and virus passaged twice on Vero E6 cells. All recombinant viruses were found to grow similarly to wild-type ZH501 in Vero E6 cell culture. To confirm the exact molecular identity of all viruses used in this Example, complete genome sequence was obtained following previously described techniques (Bird et al., *J. Virol.* 81(6):2805-2816, 2007, herein incorporated by reference).

A total of 11 separate rescue attempts using a variety of plasmid concentrations ranging from 0.5 μg to 4 μg resulted in 100% recombinant virus rescue efficiency using only the three expression plasmids.

Example 2

Generation and Characterization of Recombinant RVF (rRVF) Viruses

This example describes the generation of recombinant RVF viruses comprising deletions in the ORF of NSs and/or NSm, which play a role in viral virulence. This example further describes a recombinant RVF virus comprising a reporter gene.

RVF Virus and Biosafety

All work with infectious RVF virus (wild-type or recombinant) was conducted within the Centers for Disease Control (CDC) bio-safety level 4 (BSL-4) laboratory. Low passage (FRhL+2, Vero E6+2) working stocks of wild-type strain ZH501, isolated originally from a fatal Egyptian human case in 1977, were used as challenge virus, and were prepared by passage on Vero E6 cell monolayers. The complete genome sequence of the S, M and L segments of the wild-type RVF virus strain ZH501 has been deposited under Genbank Accession Nos. DQ380149 (SEQ ID NO: 1), DQ380200 (SEQ ID NO: 2) and DQ375406 (SEQ ID NO: 3), respectively.

Construction of ΔNSs:GFP Deletion/Replacement Plasmid

To generate plasmids containing a complete deletion of the NSs ORF, replaced by the eGFP ORF (Towner et al., *Virology* 332(1):20-27, 2005, incorporate herein by reference), the eGFP ORF was amplified by PCR with forward and reverse primers containing the KpnI (GGTACC) and BglII (AGATCT) restriction sites, respectively. Utilizing the full-length RVF S-segment plasmid (pRVS; SEQ ID NO: 11), a strand specific PCR was conducted with primers designed to contain the KpnI and BglII restriction sites annealing immediately upstream to the NSs START codon, and immediately down-stream of the NSs STOP codon. Primer sequences are shown below in Table 1. Restriction site sequences are indicated by italics.

TABLE 1

Primer sequences for replacement of NSs with eGFP

| Primer | Sequence | SEQ ID NO: |
|---|---|---|
| RVS-35/ KpnI | aaaaaa*GGTACC*GATATACTTGATAAGCACTAG | 4 |
| RVS+827/ BglII | aaaaaa*AGATCT*GATTAGAGGTTAAGGCTG | 5 |
| eGFP+1/ KpnI | aaaaaa*GGTACC*ATGGTGAGCAAGGGCGAGGAG | 6 |
| eGFP-720/ BglII | aaaaaa*AGATCT*TTACTTGTACAGCTCGTCCATG | 7 |

The resulting PCR fragment contained a complete deletion of the NSs ORF flanked by KpnI and BglII restrictions sites. The eGFP and RVF-S plasmid amplicons were gel purified and ligated following standard molecular biology techniques. The resulting plasmid (pRVS-GFPΔNSs; SEQ ID NO: 14) contained a complete in-frame replacement of the NSs ORF by eGFP.

Construction of Plasmids Containing a NSs-eGFP Fusion Protein

In a second set of plasmid constructions, rRVF viruses were generated which contained the complete full-length genome and an insertion of the eGFP ORF. Two constructions were made containing in-frame fusions of the c-terminus of NSs with the eGFP ORF, separated by amino acid linker moieties of varying lengths. In the first construction, the full-length RVF-S segment plasmid backbone was modified using site directed mutagenesis PCR (QuickChange, Stratagene) with overlapping primers (shown in Table 2 below) containing a deletion/replacement of the NSs STOP codon with a linker section containing nucleotides encoding three alanine residues and the KpnI restriction site. Following this, both this amplicon and the pRVS-GFPΔNSs plasmid were digested with KpnI. The resulting restriction enzyme fragments were gel purified and ligated to generate the final construction pRVFS-NSs(A$_3$)eGFP. A second NSs-eGFP fusion peptide construction was created to increase the length of the eGFP linker moiety and eliminate the KpnI restriction site contained in the previous fusion peptide construction. To accomplish this, site directed mutagenesis (QuickChange, Stratagene) was employed starting with the pRVFS-NSs(A$_3$)$_6$GFP backbone and overlapping primers containing the remote cutter restriction enzyme BsmBI and nucleotides encoding ten alanine residues (shown in Table 2 below).

TABLE 2

Primer sequences for construction of NSs-eGFP fusion proteins

| Primer | Sequence | SEQ ID NO: |
|---|---|---|
| RVS-829rev/ KpnI | aaaaaa*GGTACC*TGCTGCTGCATCAACCTC AACAAATCCATC | 8 |
| RVS+827/BglII | aaaaaa*AGATCT*GATTAGAGGTTAAGGCTG | 5 |
| NSsGFP+10Ala/ Fwd | aaaaaa*CGTCTC*aGCAGCAGCAGCAGCAAT GGTGAGCAAGGGCGAGGAG | 9 |
| NSsGFP+10Ala/ Rev | aaaaaa*CGTCTC*aCTGCTGCTGCTGCTGCTG CATCAACCTCAACAAATCCATC | 10 |

Following PCR amplification, restriction enzyme digestion and re-ligation, the resulting construction contained a perfect in-frame fusion of the C-terminus of NSs and eGFP ORF in the context of the complete full-length RVF S segment genome, preserving the spacing and nucleotide sequence of both the NP and NSs transcription termination signals.

Generation and In Vitro Testing of Recombinant RVF Viruses

In all cases, rescue of recombinant viruses was accomplished using cDNA plasmids encoding the virulent RVF virus ZH501 strain. The basic design and construction of the full-length plasmids containing inserts of the complete S segment (pRVS; SEQ ID NO: 11), M segment (pRVM; SEQ ID NO: 12), and L segment (pRVL; SEQ ID NO: 13), and a plasmid containing a deletion of the NSm gene (pRVMΔNSm; SEQ ID NO: 15), have been described previously (Bird et al., *Virology* 362:10-15, 2007; Gerrard et al., *Virology* 359:459-465, 2007, each of which is herein incorporated by reference). Maps of the full-length S, M and L plasmids, and plasmids containing NSs and NSm deletions, are shown in FIGS. 5-9.

Anti-genomic sense plasmids representing the three genomic segments were transfected in 1 μg quantities with LT-1 (Minis) at a ratio of 6:1 and transferred onto sub-confluent (approximately 60-70% confluent) monolayers of BSR-T7/5 cells stably expressing T7 polymerase (Buchholz et al., *J. Virol.* 73(1):251-259, 1999, herein incorporated by reference). Four or five days post transfection, the cell supernatant was clarified by low speed centrifugation and passaged twice on confluent monolayers of Vero E6 cells. After passage and prior to use in subsequent experiments, the complete genome sequence of each rescued recombinant virus was confirmed by previously described techniques (Bird et al., *J. Virol.* 81:2805-2816, 2007, herein incorporated by reference).

Infected Live Cell (Direct) or Fixed Cell (Indirect) Fluorescent Antibody Detection of RVF NSs and eGFP Proteins Vero E6 cells were seeded on glass coverslips and infected at a multiplicity of infection (MOI) of approximately 1.0 with either rZH501-ΔNSs:GFP, rZH501-ΔNSs: GFP-ΔNSm, rZH501-NSs(Ala)$_3$GFP or rZH501—NSs(Ala)$_{10}$GFP. At 24 hours post infection, cells were directly visualized by inverted ultraviolet microscopy (live cell) or were fixed in 10% formalin overnight. Following fixation, infected cells were gamma-irradiated ($5.0 \times 10^6$ RAD) to inactivate any residual virus activity. After inactivation, cells were permeabilized (Triton X-100 0.01%) and incubated with monoclonal antibodies specific for either RVF NSs or eGFP protein following standard techniques.

Results

Rescue of all recombinant viruses used in this study was accomplished by transfection of three anti-genomic sense plasmids, each representing one of the three virus RNA segments, without the requirement of supporting expression plasmids encoding virus structural proteins. Multiple rRVF viruses were generated containing an insertion of the reporter molecule eGFP into the virus S segment (FIG. 1A). Among these, two rRVF viruses were rescued containing an in-frame fusion of the C-terminus of the NSs protein with the N-terminus of eGFP, separated by a peptide linker of either three or ten alanine residues (rZH501-NSs(Ala)$_3$GFP and rZH501-NSs(Ala)$_{10}$GFP). Two rRVF viruses were created containing deletions of either the NSs alone or NSs/NSm genes in combination (rZH501-ΔNSs:GFP and rZH501-ΔNSs:GFP-ΔNSm). In both of these viruses, the NSs gene was replaced by the reporter molecule eGFP, preserving the native S segment ambisense RNA orientation. Both rRVF viruses were rescued upon the first attempt and grew to high titers routinely exceeding $1.0 \times 10^6$ PFU/mL in Vero E6 cell culture resulting in complete monolayer lysis.

Following passage on Vero E6 cells, cytoplasmic GFP signal was first observed approximately 10-12 hours post infection and appeared to spread rapidly throughout the cell monolayer prior to the first signs of extensive CPE and plaque formation (FIG. 1B). Recombinant virus containing NSs-GFP fusion peptides (rZH501-NSs(Ala)$_3$GFP and rZH501-NSs(Ala)$_{10}$GFP) were also rescued on the first attempt but were found to grow to slightly lower titers (about $5.0 \times 10^5$ PFU/mL). NSs-GFP fusion protein was first localized in the cytoplasm of infected cells followed by perinuclear accumulation and eventual intranuclear migration followed by the formation of filamentous structures by 12-18 hours post-infection (FIGS. 1B and 1C) Stability of the eGFP reporter gene in all recombinant viruses reported here was followed for 15 serial passages (1:100 dilution between each passage) in Vero E6 cells during which time no decrease in the stability of eGFP expression was observed, with all infected cells expressing robust amounts of eGFP protein similar to that seen in early passages.

Example 3

In Vivo Immunogenicity and Safety of rRVF Viruses

This example describes a study to determine the immunogenicity and safety of the recombinant RVF viruses described in the examples above.

Animal Immunization and Infection

A total of 66 female Wistar-furth (WF/NSd) (Harlan) rats 6-8 weeks of age (approximately 160 g) were used in this study. The animals were housed in micro-isolator pans and provided food and water ad libitum. All pans were kept in HEPA filtration racks following standard barrier care techniques within the BSL-4 laboratory for the duration of the experiment. All animals were inoculated subcutaneously (SQ) in the right hind flank with an inoculum (vaccine or challenge virus) prepared in 200 μL of sterile physiologic saline. A total of eight animals that were administered sterile saline only served as sham inoculated animal controls (three in the pilot study, five in the vaccination/challenge study). All animals were examined daily post inoculation for signs of clinical illness, weight loss and respiratory distress. Animals found either in distress or moribund were immediately anesthetized using isoflurane and then euthanized using Beuthanasia solution (Schering-Plough) following standard techniques.

Pilot In Vivo Immunogenicity and Safety Study

A total of 18 rats were administered $1.0 \times 10^3$ PFU SQ of either the rZH501-ΔNSs:GFP (nine animals) or rZH501-ΔNSs:GFP-ΔNSm (nine animals) with three animals serving as sham inoculated controls. Following vaccination, a small (approximately 25 μL) sample of whole blood was obtained via the tail vein on days 1-4 to detect vaccine virus induced viremia. This whole blood sample was placed directly into 2× non-cellular lysis buffer (Applied Biosystems) for decontamination and transfer to a BSL-2 laboratory following standard protocols (Towner et al., *J. Infect. Dis.* S2002-S212, 2007, incorporated herein by reference) for subsequent RNA extraction and RVF specific q-RT-PCR. At day 21 post-vaccination, all animals were anesthetized using isoflurane, serum samples were collected for determination of total anti-RVF IgG titers, and the animals were euthanized using Beuthanasia solution (Schering-Plough).

Anti-RVF Virus Total IgG ELISA

Determination of anti-RVF IgG titers from vaccinated and control rats was performed essentially as described by Madani et al. (*Clin. Infect. Dis.* 37:1084-1092, 2003) with the following modifications necessary for rat specimens. Standard 96-well microtiter plates were coated overnight at 4° C. with 100 μL of gamma-irradiated RVF infected Vero E6 cell lysate diluted 1:2000 in (0.01M PBS, pH 7.2), or similarly diluted gamma-irradiated uninfected Vero E6 cell lysate, to serve as adsorption controls. Plates were washed 3× (PBS 0.01% Tween-20) and 100 μL duplicate samples of rat sera were diluted 1:100-1:6400 in 4-fold dilutions in skim milk serum diluent and adsorbed for 1 hour at 37° C. Plates were washed 3× (PBS 0.01% Tween-20) and 100 μL of goat anti-Rat IgG HRP conjugate antibody (KPL, Gaithersburg, Md.) diluted 1:2500 was adsorbed for 1 hour at 37° C. After a 3× wash, 100 μL of ABTS substrate (KPL) was added and incubated for 30 minutes at 37° C.

Plates were read at 410 nm with an absorbance correction of 490 nm for plate imperfections. The absorbance of the 1:100, 1:400, 1:1600, and 1:6400 dilutions were added and constituted a SUM$_{OD}$ value for each specimen. The background adsorption of each animal serum to negative control Vero E6 cells was subtracted from the calculated SUM$_{OD}$ value obtained from antigen positive Vero E6 cells and was recorded as an adjusted-SUM$_{OD}$ value for each animal. Final end point dilution titers were determined as the reciprocal of the final serum dilution yielding an adjusted-SUM$_{OD}$ of >0.20. A cut-off value for determining positive versus negative samples was established as the mean sample adjusted-SUM$_{OD}$+3 standard deviations obtained from the five sham inoculated control animals.

Statistical Analyses

For all calculations, the analysis program XLSTAT (AddinSoft, USA) was utilized. Kaplan-Meier analyses were completed with log-rank and Wilcoxan tests of significance with an α-level setting of 0.05. Analyses of $SUM_{OD}$ and viremia were completed utilizing a one-way ANOVA and a post-hoc Tukey's HSD test of significance with an α-level setting of 0.05.

Results

To gain a primary assessment of the relative in vivo characteristics of the rZH501-ΔNSs:GFP and rZH501-ΔNSs:GFP-ΔNSm recombinant viruses, groups of nine rats were inoculated with each rRVF virus at a dose of $1.0 \times 10^3$ PFU (FIG. 4A). Animals were monitored daily for signs of clinical illness and weight loss. At no time post-vaccination did any animal show signs of clinical illness, and all experienced average daily weight changes equivalent to sham inoculated controls of approximately 0-5 g. All vaccinated rats were bled at days 1-4 post-inoculation to determine the titer of vaccine virus induced viremia. Using a highly sensitive q-RT-PCR assay, no animal at any time point analyzed post-vaccination developed a detectable viremia.

All animals were euthanized at day 21 post-vaccination and anti-RVF total IgG antibody titers were evaluated (FIG. 2). Testing revealed that the $SUM_{OD}$ (mean±SEM) for all animals vaccinated with the rZH501-ΔNSs:GFP virus was 2.14±0.12, which corresponded to end point titers of 1:1600 in 66% (%) of animals, with the remaining 33% (⅜) having titers equal to 1:400. Among animals receiving the rZH501-ΔNSs:GFP-ΔNSm virus, $SUM_{OD}$ (mean±SEM) was 1.24±0.06, with 89% (%) developing end-point dilution titers equal to 1:400. As expected, all sham-inoculated animals (N=3) were negative for detectable levels of anti-RVF total IgG antibody $SUM_{OD}$-0.08±0.06. All vaccinated animals in the rZH501-ΔNSs:GFP and rZH501-ΔNSs:GFP-ΔNSm virus groups developed statistically higher mean anti-RVF total IgG $SUM_{OD}$ values compared with non-vaccinated controls (p-value <0.001 and p-value=0.003, respectively). Animals in the rZH501-ΔNSs:GFP virus group developed significantly higher mean $SUM_{OD}$ values than animals given the rZH501-ΔNSs:GFP-ΔNSm vaccine (p-value=0.004). Plaque reduction neutralization titers ($PRNT_{50}$) testing was completed on a subset (four animals) chosen randomly from each vaccine virus group with two sham inoculated animals serving as controls. The results showed mean $PRNT_{50}$ titers of 1:1480 (rZH501-ΔNSs:GFP) and 1:280 (rZH501-ΔNSs:GFP-ΔNSm), with sham inoculated control animal titer of ≤1:10.

Example 4

Follow-Up Vaccination and Virulent Virus Challenge Study

This example describes the efficacy of recombinant RVF viruses comprising a deletion in the NSs ORF, or comprising a deletion in both the NSs and NSm ORFs, following challenge with wild-type virus.

Vaccination and Virus Challenge

A total of 20 rats were vaccinated in two dosage groups of ten animals each with either $1.0 \times 10^3$ or $1.0 \times 10^4$ PFU SQ of the rZH501-ΔNSs:GFP virus as described above. An additional 20 rats were inoculated in two dosage groups of ten animals each with either $1.0 \times 10^3$ or $1.0 \times 10^4$ PFU SQ of the rZH501-ΔNSs:GFP-ΔNSm virus as described above. A total of five animals served as sham inoculated controls. On days 2, 4 and 7 post-vaccination, a small blood sample (approximately 25 µL) was collected from the tail vein and added directly to 2× non-cellular lysis buffer (Applied Biosystems) as described above for subsequent RNA extraction and q-RT-PCR.

At day 26 post-vaccination, all animals were briefly anesthetized using isoflurane vapor (3.0-3.5% atmosphere) ($RC^2$ Rodent Anesthesia system, VetEquip) and a 500 µL sample of whole blood was obtained. Serum was collected and stored at −70° C. for later determination of total anti-RVF IgG titers, $PRNT_{50}$ and anti-NSs/anti-NP specific antibody. All serum samples were surface decontaminated and inactivated by gamma-irradiation ($5.0 \times 10^6$ RAD) following standard BSL-4 safety protocols prior to use in a BSL-2 laboratory.

At day 28 post-vaccination, all rats (vaccinated and sham controls) were challenged with $1.0 \times 10^3$ PFU SQ of virulent wild-type RVF virus strain ZH501, previously shown to result in lethal disease in Wistar-furth rats (Anderson et al., *Microb. Pathog.* 5:241-250, 1988; Anderson et al., *Am. J. Trop. Med. Hyg.* 44(5):475-80, 1991; Bird et al., *Virology* 362:10-15, 2007, each of which is herein incorporated by reference). On days 2, 3, 4 and 7 following challenge, a small blood sample was collected from the tail vein for subsequent RNA extraction and RVF specific q-RT-PCR to assess the level of viremia. At day 42 post-challenge, all animals surviving wild-type virus infection were bled via cardiac puncture under general anesthesia (isoflurane vapor, $RC^2$ Rodent Anesthesia system, VetEquip) followed by euthanasia (Beuthanasia solution, Schering-Plough).

Anti-RVF Virus Plaque Reduction and Neutralization Testing ($PRNT_{50}$)

The stock of RVF virus was diluted to 50 PFU in 300 µL of DMEM (1% Penicillin/Streptomycin) without FBS. Separately, aliquots of serum from vaccinated rats or from sham inoculated controls corresponding to 21 days post-vaccination (pilot study) or 26 days (challenge study) were heat inactivated for 30 min at 56° C. After inactivation, serum dilutions of 1:10, 1:40, 1:160, 1:640, 1:2560 and 1:10240 were made in DMEM (1% Pen/Strep). Diluted rat serum (300 µL) was mixed with an equal volume of diluted virus and incubated overnight at 4° C. The following day, each mixture of serum+RVF virus was used to infect confluent monolayers of Vero E6 cells in 12-well plates. After a 1 hr adsorption, the mixture was removed and a 1-2 ml nutrient agarose overlay (MEM 1×, 2% FBS, 1% Pen/Strep, 1% SeaPlaque agar) was added to the monolayers. After a five-day incubation, the cells were fixed with 10% formalin overnight. Following fixation, the agarose overlay was removed and the plates were surface decontaminated and gamma-irradiated ($2.0 \times 10^6$ RAD) following standard BSL-4 safety procedures. After inactivation, the cell monolayer was stained with 1% crystal violet in PBS and plaques were enumerated. The calculated $PRNT_{50}$ titers correspond to the reciprocal titer of the last dilution resulting in a 50% reduction in the number of plaques when compared to controls.

RVF Virus Specific q-RT-PCR

Whole rat blood was assayed for the presence and quantity of RVF specific virus RNA as described previously (Bird et al., *J. Clin. Microbiol.* 45(11):3506-13, 2007, incorporated herein by reference). Quantification of total serum RVF RNA was calculated directly via interpolation from a standard curve generated from serial dilutions of stock RVF virus strain ZH501 of a known titer in whole rat blood extracted and processed in an identical manner with each experimental replicate q-RT-PCR run. Briefly, 25 µL of whole rat blood (either from vaccinated/challenged animals or stock virus serial dilutions) was added to 300 µL 2× non-cellular lysis buffer (Applied Biosystems) and total RNA was extracted (ABI 6100 nucleic acid workstation, Applied Biosystems.) After extraction, cDNA was generated by random hexamer priming (High Capacity cDNA kit, Applied Biosystems) followed by RVF specific q-PCR (Universal q-PCR master mix, Applied Biosystems). Results are reported as RVF PFU equivalents/mL of rat blood.

Results

Immunization Phase

Following the promising findings of robust immunogenicity and in vivo attenuation in the initial pilot study, a larger study was undertaken utilizing multiple doses of each recombinant RVF virus followed by virulent virus challenge. Groups of ten animals each were inoculated with either rZH501-ΔNSs:GFP or rZH501-ΔNSs:GFP-ΔNSm viruses at dosages of $1.0 \times 10^3$ or $1.0 \times 10^4$ PFU (FIG. 4B). Whole blood samples were assayed at day 2, 4, and 7 post-vaccination for the presence of detectable viremia. As was observed in the pilot study, at no time did any animal develop detectable vaccine viremia. Additionally, no clinical illness was observed among any vaccinated animals, and all experienced weight gains of approximately 1-5 g per day, similar to sham inoculated controls.

At day 26 post-vaccination, serum samples were obtained to determine the level of total anti-RVF IgG, $PRNT_{50}$, and anti-NP/anti-NSs protein specific antibody production prior to subsequent challenge on day 28. All animals regardless of recombinant virus type or dose, developed high-titered total anti-RVF IgG antibody (FIG. 2). Among rats receiving the rZH501-ΔNSs:GFP virus, the mean $SUM_{OD} \pm SEM$ was $4.10 \pm 0.12$ ($1.0 \times 10^3$ dose group) and $4.79 \pm 0.11$ ($1.0 \times 10^4$ dose group), which corresponded to 85% (17/20) of animals developing anti-RVF IgG end-point titers of 1:6400. The remaining three animals in the rZH501-ΔNSs:GFP virus group developed end-point titers equal to 1:1600. In animals receiving the rZH501-ΔNSs:GFP-ΔNSm virus, the mean $SUM_{OD} \pm SEM$ was $3.94 \pm 0.12$ ($1.0 \times 10^3$ dose group) and $4.54 \pm 0.11$ ($1.0 \times 10^4$ dose group), which corresponded to 75% (15/20) developing anti-RVF IgG end-point titers of 1:6400, with the remaining 25% (5/20) attaining end-point titers of 1:1600. As was observed in the pilot study, all animals vaccinated with either rZH501-ΔNSs:GFP or rZH501-ΔNSs:GFP-ΔNSm viruses, regardless of dose, developed statistically significant higher mean $SUM_{OD}$ values than sham inoculated control animals (p-values all <0.05).

Similarly, $PRNT_{50}$ titers were found to be elevated above sham inoculated controls among animals inoculated with the rZH501-ΔNSs:GFP virus with mean titers of 1:640 and 1:7040 in the $1.0 \times 10^3$ and $1.0 \times 10^4$ dose groups, respectively. Mean $PRNT_{50}$ titers among animals vaccinated with the rZH501-ΔNSs:GFP-ΔNSm were found to be similar with mean titers of 1:1120 and 1:640 in the $1.0 \times 10^3$ and $1.0 \times 10^4$ dose groups, respectively.

Challenge Phase

On day 28 post-vaccination, all rats were challenged with a known lethal dose ($1.0 \times 10^3$ PFU) of virulent wild-type strain ZH501. All animals were monitored daily for signs of clinical illness and weight loss/gain for 42 days post-challenge. At no time post challenge (days 1-42) did any rat that received prior vaccination with either the rZH501-ΔNSs:GFP or rZH501-ΔNSs:GFP-ΔNSm viruses develop clinically detectable illness (ruffled fur, hunched posture or lethargy). At approximately day 2 post-challenge, a majority of animals suffered slight 1-5 g reductions in total body weight that was regained by day 5 post-challenge.

Rat whole blood was obtained on days 2, 3, 4 and 7 post-challenge and assayed for the presence of RVF virus RNA by a highly sensitive q-RT-PCR assay (Bird et al., *J. Clin. Microbiol.* 45(11):3506-13, 2007, incorporated herein by reference). Following challenge, low-level viremia was detected in a total of 3/40 vaccinated animals. Among the 20 animals that were vaccinated with rZH501-ΔNSs:GFP-ΔNSm, two animals developed a peak post-challenge viremia on day 3 of $1.1 \times 10^2$ and $7.0 \times 10^1$ PFU equivalents/mL of whole blood, respectively (FIG. 4B). In the 20 animals vaccinated with rZH501-ΔNSs:GFP, one animal was detected with a peak post-challenge viremia on day 4 of $1.5 \times 10^1$ PFU equivalents/mL of whole blood. In all three animals, the detectable viremia was transient and was resolved by day 7 post-challenge. No other vaccinated animals (37 total) had a detectable RVF virus viremia at any time point assayed post challenge. In sharp contrast, the five sham inoculated animals all suffered severe to lethal clinical illness with 3/5 animals succumbing to infection by day 3 post-challenge with peak viremia titers of $1.9 \times 10^7$, $2.7 \times 10^7$, and $3.1 \times 10^7$ PFU equivalents/mL. Two sham-inoculated animals did not succumb to infection but did develop severe clinical illness (ruffled fur, hunched back, lethargy) with a peak viremia post-challenge of $2.7 \times 10^4$ and $5.8 \times 10^3$ PFU equivalents/mL whole blood. As anticipated, both candidate vaccines (rZH501-ΔNSs:GFP or rZH501-ΔNSs:GFP-ΔNSm) significantly reduced post-challenge viremia (p-value <0.0001) regardless of dose. Additionally, Kaplan-Meier survivor analysis (log-rank and Wilcoxan tests) of survival post-challenge revealed a significant protective efficacy effect with both rRVF viruses regardless of dose when compared with sham-inoculated controls (p-value <0.001).

Example 5

Differentiation of Wild Type-Infected and Vaccinated Animals

This example describes how rRVF viruses lacking NSs can be used to differentiate animals that have been infected with the rRVF virus and wild-type virus using methods to detect antibodies specific for NSs and NP.

Anti-RVF NSs and NP Differential Indirect Fluorescent Antibody (IFA) Assays

Plasmid constructions expressing only the RVF nucleoprotein (NP) or non-structural S(NSs) proteins were generated following techniques described previously (Niwa et al., *Gene* 108:193-199, 1991, incorporated herein by reference). Briefly, oligonucleotide primers were designed to anneal within the NP or NS s ORF with the addition of a SacI and BglII restriction site for cloning into a polymerase II-based expression plasmid, pCAGGS. The resulting PCR amplicons were agarose gel purified, digested with SacI and BglII, and ligated between the corresponding restriction sites of the pCAGGS vector. Prior to use, the resulting clones, pC-NP and pC-NSs, were sequenced using standard techniques.

Following confirmation of the molecular sequence, each plasmid was transfected separately on Vero E6 cells grown on glass coverslips in 1 μg quantities at a 6:1 ratio with lipofectant solution (LT-1, Minis). Following a 48-hour incubation, transfected cells expressing either the NP or NSs protein were fixed with 10% formalin. To assess the presence or absence of anti-NP or anti-NSs antibody, serum samples from all vaccinated and the two surviving sham inoculated control animals were adsorbed separately for 1 hour on cells transfected with either NP or NSs. The presence or absence of anti-NP or anti-NSs adsorbed rat antibody was visualized by secondary adsorption of an AlexaFluor 594 nm (Giorgi et al., *Virology* 180:738-753, 1991) anti-rat total IgG (Molecular Probes/Invitrogen) antibody. Intra-nuclear localization of NSs protein and rat antibody was confirmed by DAPI counterstaining. To confirm the presence of anti-RVF virus NP and NSs antibodies among naturally infected animals, archived serum samples collected from goats in Saudi Arabia during the outbreak in 2000 were tested essentially as described above with anti-goat specific total IgG (AlexaFluor 488 nm, FITC, Molecular Probes/Invitrogen).

Results

Serum obtained from all vaccinated and sham vaccinated animals at day 26 post-vaccination was tested for the presence of anti-NP and anti-NSs specific antibodies utilizing Vero E6 cells transfected with plasmids expressing either NP or NSs proteins. As a positive control, the serum obtained from the two sham vaccinated animals that survived infection, and six additional control rat serum samples (taken from animals inoculated with a sub-lethal dose of RVF virus for validation purposes) were utilized. Control animals surviving infection developed high levels of both anti-NP and anti-NSs antibody with strong immunostaining of both in vitro expressed cytoplasmic NP and filamentous intra-nuclear accumulations of NSs protein (FIG. 3A). No anti-NS or anti-NP antibodies were detected in serum from control rats (FIG. 3C). In concordance with the anti-RVF total IgG data, all vaccinated animals demonstrated high anti-NP specific antibody levels, and as anticipated, no vaccinated animal, regardless of vaccine virus or dose, developed detectable anti-NSs specific antibody (FIG. 3B). As a further step toward the demonstration of the ability to differentiate naturally infected animals from those vaccinated with the vaccines provided herein, naturally infected livestock were also shown to produce anti-NSs antibodies similar to those observed with the wild type virus infected rats (FIG. 3D).

Example 6

Safety and Efficacy of Recombinant RVF Virus Vaccines in Pregnant Ewes

The safety and efficacy of recombinant RVF virus vaccines can be evaluated in pregnant ewes according to procedures well known in the art (Morrill et al., Am. J. Vet. Res. 48(7):1042-1047, 1987; Baskerville et al., Res. Vet. Sci. 52:307-311, 1992, each of which is herein incorporated by reference). By way of example, rRVF viruses are evaluated in healthy, RVF virus sero-negative, crossbred ewes at approximately 12 weeks gestation. The ewes are housed in a biological containment facility and fed a daily ration of alfalfa hay and a commercial grain mix ration, with grass hay and water provided ad libitum. Pregnant ewes are administered recombinant RVF virus subcutaneously or intramuscularly at various doses. Mock-infected ewes serve as controls. Ewes are monitored daily for health. At various time points post-inoculation, blood, serum or other body fluid samples can be taken to assay RVF virus-induced viremia or anti-RVF virus antibody production as described above, or other desired biological endpoints. Lambs born to inoculated ewes are allowed to remain with their dams and suckle.

To test efficacy of the recombinant RVF viruses as vaccines, inoculated and sham-inoculated ewes are administered wild-type RVF virus at various doses. Lambs can also be challenged with live virus to determine whether maternal antibodies against recombinant RVF virus provide protection against natural infection. Animals are observed daily for signs of clinical illness, weight loss and respiratory distress. Animals that are in distress or moribund are immediately anesthetized and then euthanized. As described above, at various time points following inoculation, small blood samples can be taken to test for the presence of viral RNA. Serum samples can be collected to determine anti-RVF virus antibody titers.

Example 7

Safety and Efficacy of Recombinant RVF Virus Vaccines in a Rhesus Macaque Model for Human Disease The safety and efficacy of recombinant RVF virus vaccines can be evaluated in non-human primates, such as rhesus macaques, according to procedures well known in the art (Morrill and Peters, *Vaccine* 21:2994-3002, 2003). By way of example, rRVF viruses are evaluated in adult (5-10 kg) and/or juvenile (1-3 kg) captive-bred rhesus monkeys (*Macaca mulatta*). Animals are housed in individual cages in a biosafety level 3 (BSL-3) biological containment facility maintained at constant room temperature with a 12 hour light/dark photoperiod. Inoculations are given, and rectal temperatures and venous blood samples are taken while the animals are under ketamine-xylazine anesthesia.

Sero-negative monkeys are inoculated intravenously or intramuscularly with various doses of recombinant RVF viruses. Mock-inoculated animals serve as controls. The animals are monitored daily for clinical signs of illness, including weakness, paralysis or any alteration of physical condition. At various time points post-inoculation, blood, serum or other body fluid samples can be taken to assay RVF virus-induced viremia, anti-RVF virus antibody production, or other desired biological endpoints (for example, white blood cell count, red blood cell count, hematocrit, platelet count, AST and ALT). Moribund monkeys are euthanized and necropsied.

To test efficacy of the recombinant RVF viruses as vaccines, inoculated and sham-inoculated monkeys are administered wild-type RVF virus at various doses. Animals are observed daily for signs of clinical illness, weight loss and respiratory distress. Animals that are in distress or moribund are immediately anesthetized and then euthanized. As described above, at various time points following inoculation, small blood samples can be taken to test for the presence of viral RNA. Serum samples can be collected to determine anti-RVF virus antibody titers.

Example 8

Vaccination of Human Subjects with Recombinant RVF Virus

The safety and efficacy of recombinant RVF virus vaccines can be evaluated in human volunteers according to procedures well known in the art (Pittman et al., *Vaccine* 18:181-189, 2000, herein incorporated by reference). Typically, human volunteers are selected from those having occupations that put them at risk of infection with RVF virus, such as veterinarians in endemic areas. All volunteers are screened to ensure they are in good health. Informed consent is obtained from each volunteer prior to vaccination.

In this example, human volunteers are injected with candidate rRVF vaccine subcutaneously at an appropriate dose. The appropriate dose is the dose approved by the FDA, and can be determined from suitable animal studies conducted prior to human vaccination trials. Other routes of administration are possible, including intramuscular and intravenous. The vaccine can be administered as a single dose, or given in multiple doses, such as two, three or four doses. When administered in multiple doses, the booster doses can be administered at various time intervals, such as months to years. Serum samples can be obtained to determine neutralizing antibody titers and identify responder and non-responders to the vaccine.

Vaccinated volunteers are encouraged to return and report local or systemic reactions. Local reactions are assessed by grading pain and tenderness at the site of inoculation and/or axillary lymph nodes and measuring erythema and induration at the site. Systemic reaction parameters include fever, chills, headache, malaise, myalgia, arthralgia, sore throat, gastric upset, dizziness, photophobia and skin rash. Additional laboratory samples, including complete blood cell count, chemistry profile, β-HCG (in females), urinalysis, blood samples for viremia titrations, and oropharyngeal washing for viral isolated culture can be obtained. Using serum samples obtained from vaccinated individuals, plaque-reduction neutralization tests can be performed to determine how robust the immune response was to the particular rRVF virus. Vaccinated volunteers are also screened for the development of RVF virus infection.

This disclosure provides recombinant RVF viruses comprising deletions in virus virulence genes. The disclosure further provides methods of immunizing subjects at risk of infection with RVF virus with the recombinant viruses. It will be apparent that the precise details of the methods described may be varied or modified without departing from the spirit of the described disclosure. We claim all such modifications and variations that fall within the scope and spirit of the claims below.

The invention claimed is:

1. A recombinant Rift Valley fever (RVF) virus, wherein the genome of the recombinant RVF virus comprises
   a full-length L segment; an M segment comprising a complete deletion of the NSm open reading frame (ORF); and an S segment comprising a complete deletion of the NSs ORF.

2. The recombinant RVF virus of claim 1, wherein the full-length L segment is a RVF virus strain ZHSO1 L segment.

3. The recombinant RVF virus of claim 1, wherein the nucleotide sequence of the L segment is at least 95% identical to the nucleotide sequence of SEQ ID NO: 3.

4. The recombinant RVF virus of claim 3, wherein the nucleotide sequence of the L segment comprises the nucleotide sequence of SEQ ID NO: 3.

5. The recombinant RVF virus of claim 1, wherein the NSs ORF is replaced by the ORF of a reporter gene.

6. The recombinant RVF virus of claim 5, wherein the reporter gene encodes a green fluorescent protein.

7. An immunogenic composition comprising the recombinant RVF virus of claim 1 and a pharmaceutically acceptable carrier.

8. A method of eliciting an immune response in a subject against RVF virus, comprising administering to the subject the immunogenic composition of claim 7.

9. The method of claim 8, wherein the subject is livestock.

10. The method of claim 8, wherein the subject is a human.

* * * * *

UNITED STATES PATENT AND TRADEMARK OFFICE
CERTIFICATE OF CORRECTION

| | |
|---|---|
| PATENT NO. | : 9,439,935 B2 |
| APPLICATION NO. | : 14/163058 |
| DATED | : September 13, 2016 |
| INVENTOR(S) | : Bird et al. |

It is certified that error appears in the above-identified patent and that said Letters Patent is hereby corrected as shown below:

On the Title Page

Item (54) and in the Specification, Column 1, Lines 1-2, "RECOMBINANT RIFT VALLEY FEVER (RVF) VIRUSES AND METHODS" should read –RECOMBINANT RIFT VALLEY FEVER (RVF) VIRUSES AND METHODS OF USE–

Signed and Sealed this
Third Day of January, 2017

Michelle K. Lee
*Director of the United States Patent and Trademark Office*